(12) United States Patent
Zhang et al.

(10) Patent No.: US 9,066,986 B2
(45) Date of Patent: Jun. 30, 2015

(54) ANTI-CEACAM6 ANTIBODIES AND USES THEREOF

(75) Inventors: Jianbing Zhang, Ottawa (CA); Toya Nath Baral, Ottawa (CA); Yanal Murad, Ottawa (CA)

(73) Assignee: National Research Council of Canada, Ottawa, ON ( * ) Notice: Subject to any disclaimer, the term of this patent is extended or adjusted under 35 U.S.C. 154(b) by 116 days.

(21) Appl. No.: 13/876,609

(22) PCT Filed: Sep. 30, 2011

(86) PCT No.: PCT/CA2011/001081
§ 371 (c)(1),
(2), (4) Date: Mar. 28, 2013

(87) PCT Pub. No.: WO2012/040824
PCT Pub. Date: Apr. 5, 2012

(65) Prior Publication Data
US 2013/0272958 A1  Oct. 17, 2013

Related U.S. Application Data

(60) Provisional application No. 61/388,746, filed on Oct. 1, 2010, provisional application No. 61/514,618, filed on Aug. 3, 2011.

(51) Int. Cl.
| C07K 16/30 | (2006.01) |
| A61K 51/00 | (2006.01) |
| G01N 33/53 | (2006.01) |
| A61K 51/10 | (2006.01) |
| C07K 14/705 | (2006.01) |
| G01N 33/574 | (2006.01) |

(52) U.S. Cl.
CPC ......... *A61K 51/1093* (2013.01); *A61K 51/1048* (2013.01); *C07K 14/70503* (2013.01); *C07K 16/3007* (2013.01); *C07K 2317/569* (2013.01); *C07K 2317/92* (2013.01); *G01N 33/57473* (2013.01); *G01N 33/57492* (2013.01); *C07K 2317/22* (2013.01); *C07K 2317/34* (2013.01); *C07K 2317/52* (2013.01); *C07K 2317/64* (2013.01)

(58) Field of Classification Search
CPC ........... C07K 16/3007; C07K 2317/22; C07K 2317/569; C07K 2317/34; A61K 51/1048; A61K 51/1093; G01N 33/574; G01N 33/57473; G01N 33/57492
See application file for complete search history.

(56) References Cited

U.S. PATENT DOCUMENTS

| 5,693,761 | A | 12/1997 | Queen et al. |
| 5,766,886 | A | 6/1998 | Studnicka et al. |
| 5,821,123 | A | 10/1998 | Studnicka |
| 5,859,205 | A | 1/1999 | Adair et al. |
| 5,869,619 | A | 2/1999 | Studnicka |
| 6,054,297 | A | 4/2000 | Carter et al. |
| 6,180,370 | B1 | 1/2001 | Queen et al. |
| 8,404,812 | B2 * | 3/2013 | Song et al. ............ 530/387.1 |

FOREIGN PATENT DOCUMENTS

| EP | 519596 | 12/1992 |
| EP | 626390 | 11/1994 |
| WO | 95/04069 | 2/1995 |
| WO | 03/046560 | 6/2003 |
| WO | 2004/076670 | 9/2004 |

OTHER PUBLICATIONS

Cheng et al., Eur. J. Cancer 2014; 50:713-21.*
Baral et al., J. Immunol Methods 2011; 371:70-80.*
Strome et al., The Oncologist, 2007; 12:1084-95.*
Cai et al. J. Nucl. Med. 2007; 48:304-10.*
Sundaresan et al., J. Nucl. Med, 2003; 44:1962-69.*
National Cancer Institute (NCI) at the Institutes of Health Tumor Markers Fact Sheet, updated Dec. 2011; available at www.cancer.gov/cancertopics/factsheet/detection/tumor-markers, last visited Sep. 17, 2014.*
McShane et al., Nature Clinical Practice Oncology 2005; 2:416-22.*
Barnich et al. J Clin. Invest. 2007; 117:1566-74.*
Extended European Search Report dated Feb. 6, 2014 for corresponding EP Appln No. 11827851.4.
Toya Nath Baral et al, Isolation of functional single domain antibody by whole cell immunization: Implications for cancer treatment, Journal of Immunological Methods, vol. 371, No. 1, Jun. 2011, pp. 70-80.
Gang Niu et al, Molecular targeting of CEACAM6 using antibody probes of different sizes, Journal of Controlled Release, vol. 161, No. 1, Apr. 2012, pp. 18-24.
Schoelzel S et al, Carcinoembryonic antigen family members CEACAM6 and CEACAM7 are differentially expressed in normal tissues and oppositely deregulated in hyperplastic colorectal polyps and early adenomas, American Journal of Pathology, vol. 156, No. 2, Feb. 2000, pp. 595-605.
Arbabi-Ghahroudi M., A. Desmyter, L. Wyns, R. Hamers, and S. Muyldermans, Selection and identification of single domain antibody fragments from camel heavy-chain antibodies. FEBS Lett 414 (1997) 521-526.
Arbabi-Ghahroudi M, To R, Gaudette N, Hirama T, Ding W, MacKenzie R, Tanha J. Aggregation-resistant VHs selected by in vitro evolution tend to have disulfide-bonded loops and acidic isoelectric points. Protein Eng Des Sel 2009;22:59-66.
Armstrong T, Packham G, Murphy LB, et al. Type I Collagen Promotes the Malignant Phenotype of Pancreatic Ductal Adenocarcinoma. Clinical Cancer Research 2004;10:7427-37.

(Continued)

*Primary Examiner* — Sheela J Huff
*Assistant Examiner* — Jessica H Roark
(74) *Attorney, Agent, or Firm* — Sonia Patenaude

(57) ABSTRACT

The present invention relates to isolated or purified antibodies or fragments thereof specific for CEACAM6 and their use as therapeutic or diagnostic tools. Specifically, the present invention is directed to antibodies or fragments thereof specific for a linear epitope of CEACAM6. In vivo and in vitro methods of diagnosis as well as therapeutic methods are also described.

23 Claims, 19 Drawing Sheets

(56) References Cited

OTHER PUBLICATIONS

Baselga J, Tripathy D, Mendelsohn J, Baughman S, Benz CC, Dantis L, Sklarin NT, Seidman AD, Hudis CA, Moore J, Rosen PP, Twaddell T, et al. Phase II study of weekly intravenous trastuzumab (Herceptin) in patients with HER2/neu-overexpressing metastatic breast cancer. Semin Oncol 1999;26:78-83.
Bell, A., Wang, Z.J., Arbabi-Ghahroudi, M., Chang, T.A., Durocher, Y., Trojahn, U., Baardsnes, J., Jaramillo, M.L., Li, S., Baral, T.N., O'Conner-McCourt, M., Mackenzie, R. and Zhang, J. Differential tumor-targeting abilities of three single-domain antibody formats. Cancer Lett. 289, 81-90 (2010).
Blumenthal RD, Hansen HJ, Goldenberg OM. Inhibition of adhesion, invasion, and metastasis by antibodies targeting CEACAM6 (NCA-90) and CEACAM5 (Carcinoembryonic Antigen). Cancer Res 2005;65:8809-17.
Blumenthal RD, LeonE, Hansen HJ, Goldenberg OM. Expression patterns of CEACAM5 and CEACAM6 in primary and metastatic cancers. BMC Cancer 2007;7:2.7.
Buchegger F, Schreyer M, Carrel S, Mach JP. Monoclonal antibodies identify a CEA crossreacting antigen of 95 kD (NCA-95) distinct in antigenicity and tissue distribution from the previously described NCA of 55 kD. Int J Cancer 1984;33:643-9.
Davies J., and L. Riechmann, Affinity improvement of single antibody VH domains: residues in all three hypervariable regions affect antigen binding. Immunotechnology 2 (1996) 169-179.
Doyle PJ, Arbabi-Ghahroudi M, Gaudette N, Furzer G, Savard ME, Gleddie S, Mclean MD, Mackenzie CR, Hall JC. Cloning, expression, and characterization of a single-domain antibody fragment with affinity for 15-acetyl-deoxynivalenol. Mol Immunol 2008;45:3703-13.
Dumoulin m., K. Conrath, A. Van Meirhaeghe, F. Meersman, K. Heremans, L.G. Frenken, et al., Single-domain antibody fragments with high conformational stability. Protein Sci 11 (2002) 500-515.
Durocher, Y., S. Perret, et al. (2002). "High-level and high-throughput recombinant protein production by transient transfection of suspension-growing human 293-EBNA 1 cells." Nucleic Acids Res 30(2): E9.
Duxbury MS, Ito H, Benoit E, Ashley SW, Whang EE. CEACAM6 is a determinant of pancreatic adenocarcinoma cellular invasiveness. Br J Cancer 2004a;91:1384-90.
Duxbury MS, Ito H, Benoit E, Waseem T, Ashley SW, Whang EE. A novel role for carcinoembryonic antigen-related cell adhesion molecule 6 as a determinant of gemcitabine chemoresistance in pancreatic adenocarcinoma cells. Cancer Res 2004b;64:3987-93.
Duxbury MS, Ito H, Ashley SW, Whang EE. CEACAM6 cross-linking induces caveolin-1-dependent, Src-mediated focal adhesion kinase phosphorylation in BxPC3 pancreatic adenocarcinoma cells. J Bioi Chem 2004c;279:23176-82.
Duxbury MS, Ito H, Ashley SW, Whang EE. c-Src-dependent crosstalk between CEACAM6 and alphavbeta3 integrin enhances pancreatic adenocarcinoma cell adhesion to extracellular matrix components. Biochem Biophys Res Commun 2004d;317:133-41.
Duxbury MS, Matros E, Ito H, Zinner MJ, Ashley SW, Whang EE. Systemic siRNAmediated gene silencing: a new approach to targeted therapy of cancer. Ann Surg 2004f;240:667-7 4; discussion 75-6.
Els Conrath K, Lauwereys M, Wyns L, Muyldermans S. Camel single-domain antibodies as modular building units in bispecific and bivalent antibody constructs. J Bioi Chem 2001;276:7346-50.
Fedarovich A, Tomberg J, Nicholas RA, Davies C. Structure of the N-terminal domain of human CEACAM1: binding target of the opacity proteins during invasion of *Neisseria meningitidis* and *N. gonorrhoeae*. Acta Crystallogr D Bioi Crystallogr 2006;62:971-9.
Giannopoulos G, Pavlakis K, Parasi A, et al. The Expression of Matrix Metalloproteinases-2 and -9 and their Tissue Inhibitor 2 in Pancreatic Ductal and Ampullary Carcinoma and their Relation to Angiogenesis and Clinicopathological Parameters. Anticancer Research 2008;28: 1875-81.
Han F, Zhu H-G. Caveolin-1 Regulating the Invasion and Expression of Matrix Metalloproteinase (MMPs) in Pancreatic Carcinoma Cells. The Journal of surgical research 2010;159:443-50.
Haq M, Shafii A, Zervos EE, Rosemurgy AS. Addition of matrix metalloproteinase inhibition to conventional cytotoxic therapy reduces tumor implantation and prolongs survival in murine model of human pancreatic cancer. Cancer Res 2000;60:3207-11.
Kessenbrock K, Plaks V, Werb Z. Matrix Metalloproteinases: Regulators of the Tumor Microenvironment. Cell 2010;141:52-67.
Lefranc, M.-P. et al.,(2003) Dev. Comp. Immunol., 27, 55-77.
Kunnumakkara AB, Sung B, Ravindran J, et al. {Gamma}-tocotrienol inhibits pancreatic tumors and sensitizes them to gembitabine treatment by modulating the inflammatory microenvironment. Cancer Res 2010;70:8695-705.
Lewis-Wambi JS, Cunliffe HE, Kim HR, Willis AL, Jordan VC. Overexpression of CEACAM6 promotes migration and invasion of oestrogen-deprived breast cancer cells. Eur J Cancer 2008;44:1770-9.
Li S, Zheng W, Kuolee R, Hirama T, Henry M, Makvandi-Nejad S, Fjallman T, Chen W, Zhang J. Pentabody-mediated antigen delivery induces antigen-specific mucosal immune response. Mol Immunol 2009;46: 1718-26.
Mosmann T. Rapid colorimetric assay for cellular growth and survival: application to proliferation and cytotoxicity assays. J Immunol Methods 1983;65:55-63.
Ordonez C, Screaton RA, Ilantzis C, Stanners CP. Human carcinoembryonic antigen functions as a general inhibitor of anoikis. Cancer Res 2000;60:3419-24.
Schwarz RE, Konduri S, Awasthi N, Cafasso D, Schwarz MA. An antiendothelial combination therapy strategy to increase survival in experimental pancreatic cancer. Surgery 2009;146:241-9.
Semenza GL. Targeting HIF-1 for cancer therapy. Nat Rev Cancer 2003;3:721-32.
Strickland LA, Ross J, Williams S, Ross S, Romero M, SpencerS, Erickson R, Sutcliffe J, Verbeke C, Polakis P, van Bruggen N, Koeppen H. Preclinical evaluation of carcinoembryonic cell adhesion molecule (CEACAM) 6 as potential therapy target for pancreatic adenocarcinoma. J Pathol 2009;218:380-90.
To, R., Hirama, T., Arbabi-Ghahroudi, M., MacKenzie, R., Wang, P., Xu, P., Ni, F. and Tanha, J. Isolation of monomeric human VHs by a phage selection. J. Bioi. Chem. 280, 41395-41403 (2005).
Vogel CL, Cobleigh MA, Tripathy D, Gutheil JC, Harris LN, Fehrenbacher L, Slamon OJ, Murphy M, Novotny WF, Burchmore M, Shak S, Stewart SJ. First-line Herceptin monotherapy in metastatic breast cancer. Oncology 2001;61 Suppl 2:37-42.
Wang Z, Kong D, Banerjee S, et al. Down-regulation of Platelet-Derived Growth FactorD Inhibits Cell Growth and Angiogenesis through Inactivation of Notch-1 and Nuclear Factor-kapaB Signaling. Cancer Research 2007;67:11377-85.
Zhang J, MacKenzie R, Durocher Y. Production of chimeric heavy-chain antibodies. Methods Mol Biol 2009a;525:323-36, xv.
Zhang J, Liu X, Bell A, et al. Transient expression and purification of chimeric heavy chain antibodies. Protein Expr Purif 2009b;65:77-82.
Mai et al. (2006) ES1, a new lung carcinoma antibody—an immunological study. Histopathol. 49:515-522.

* cited by examiner

```
IMGT     <-------- FR1-IMGT --------> <CDR1-IMGT-> <--- FR2-IMGT --> <CDR2-IMGT> <-------------- FR3-IMGT --------------> <-- CDR3-IMGT ----> <-FR4-IMGT->
         1           10          20          30          40          50          60          70          80          90         100         110         120
         |********.|********|********|*********|*********|*********|*********|*********|*********|*********|*********|*********|*********|**|*********
2A3      QVKLEESGG.GLVQAGGSLRLSCRTS GRINSVYT.... MGWFRQAPGKEREFVAQ IMWGAGTNTH..YAD.SVK.GRFTISRDSAESTVYLQMNSLKPEDTAVYYC AANRGIPIAGRQVDY......WGQGTQVTVSS
         |*******.|****|*||****** *|*******|***** |**, bc|* |*abc***** |*******|******,*|abc*****| ******|*
         1          10          20          30          40          50          60          70          80          90         100         110
KABAT    <--------framework-1---------><----CDR-H1----><-framework-2--><-------CDR-H2------><----------framework-3----------><------CDR-H3------> <framework4>
```

ANTI-CEACAM6 ANTIBODIES AND USES THEREOF

CROSS-REFERENCE TO RELATED APPLICATIONS

This application is a national phase entry of International Patent Application PCT/CA2011/001081 filed Sep. 30, 2011, which claims the benefit of U.S. Provisional Patent Application Ser. No. 61/388,746 filed Oct. 1, 2010 and U.S. Provisional Patent Application Ser. No. 61/514,618 filed Aug. 3, 2011.

FIELD OF THE INVENTION

The present invention relates to anti-CEACAM6 antibodies and uses thereof. More specifically, the present invention is directed to anti-CEACAM6 antibodies and fragments thereof, and uses thereof.

BACKGROUND OF THE INVENTION

Despite advances in research and treatment, cancer remains a leading cause of death worldwide; carcinomas of the lung, breast, colon, pancreas, and ovary in particular are among those that cause the most cancer deaths per year. Treatment options for cancer patients are typically determined by the type and stage of the cancer, and can include surgery, radiation therapy, and chemotherapy. Surgery is generally preferred for localized cancers; metastasized cancers often require combination therapies. Cancer therapy with an antibody as monotherapy or in conjunction with other anti-tumor molecules is providing encouraging evidence in the fight with this chronic disease. Antibodies are also valuable molecules in the diagnosis of different cancers and may have theragnostic application. However, an ongoing need for effective treatment and diagnostic approaches for most cancers remains.

Carcinoembryonic antigen related cell adhesion molecule 6 (CEACAM6), also known as non-specific cross-reacting antigen (NCA) or CD66c, is a glycosylphosphoinositol (GPI)-linked cell surface protein and a member of the CEACAM family proteins where it shares high homology with CEACAM1, CEACAM7 and CEACAM8. CEACAM6 overexpression leads to morphology change similar to epithelium-messenchymal-transformation (Lewis-Wambi et al, 2009), increased invasivenessness (Lewis-Wambi et al, 2009), increased chemoresistance (Duxbury et al, 2004b) and resistance to anoikis (Ordonez et al, 2000). Suppression of CEACAM6 gene expression or inhibition of CEACAM6 function can reverse these effects. Expression of CEACAM6 protein has been reported in a variety of normal human tissues (Buchegger et al, 1984) including granulocytes; however, CEACAM6 expression is elevated in many solid tumors such as breast, pancreatic, ovarian, lung and colon cancer (Blumenthal et al, 2007). CEACAM6 is envisaged as a biomarker and potential therapy target for pancreatic ductal adenocarcinoma and pancreatic intraepithelial neoplasia (Duxbury et al 2004a; Duxbury et al, 2004c; Duxbury et al, 2004d), and other tumor types. Additionally, CEACAM6 over-expression in pancreatic cancer tissues promotes pancreatic cancer cell invasion, metastasis, and angiogenesis, making CEACAM6 a target for pancreatic cancer therapy.

An important feature of cancer cells is their ability to induce angiogenesis. Inhibition of tumor angiogenesis is associated with tumor growth suppression. Anti-angiogenesis agents used in therapeutic trials to treat pancreatic cancer did not yield promising results; however, it was necessary to use angiogenic inhibitors that target the angiogenesis pathway and can better enter the cancer micro-environment (Wong & Lemoine, 2009). The matrix metalloproteases (MMPs) are a family of calcium and zinc-containing enzymes involved in degradation of extracellular matrix components (ECM). In cancer, increasing extracellular proteolysis promotes cancer growth, tissue invasion, and metastasis (Kessenbrock et al, 2010). For example, in pancreatic ductal adenocarcinoma (PDA), the activity of MMPs, particularly MMP-2 and MMP-9, is increased (Giannopoulos et al, 2008). MMP-2 activity is associated with the degree of degradation of extracellular basement membrane; overexpression of MMP-9 is correlated with metastasis, invasion, and growth in pancreatic cancer ((Kessenbrock et al, 2010; Armstrong et al, 2010). It was also reported that reducing the secretion and activity of MMP-2 and MMP-9 inhibited cell invasion ability in pancreatic cancer cells (Han & Zhu, 2010). Moreover, MMP-9 plays a critical role in promoting angiogenesis for cancer growth. Down regulation of MMP-9 expression inhibits invasion and angiogenesis in pancreatic cancer cell (Wang et al, 2007). For these reasons, inhibition of MMP-2 and MMP-9 activities is an important issue for pancreatic cancer therapy.

Proteolytic degradation of extracellular matrix (ECM) is critical for cancer cell migration and for cancer cells to enter the circulation. MMP-2 and MMP-9 are expressed highly in human pancreatic cancer tissues (Haw et al, 2000). MMP-2/MMP-9 mediated extra-cellular matrix degradation leads to cancer cell invasion and metastasis. Its association with cancer progression has also been an important principle of cancer research (Kessenbrock et al, 2010). MMP-9 is associated with ECM turnover and cell migration through the ECM. It is a key enzyme that regulates cancer cell invasion and metastasis (Xu et al, 2010; Bjorklund & Koivunen et al, 2005). MMP inhibitors have been used in combination with gemcitabine to treat pancreatic cancer patients (Haq et al). In animal models, gemcitabine and MMP inhibitor combinational therapy can be used to reduce cancer implantation and improve survival compared with using gemcitabine or the inhibitor alone. However, the results of clinical trails which involved using MMP inhibitors to treat patients were not significant (Coussens et al, 2002; Longo et al, 2008).

Previous studies have demonstrated tumor growth inhibition can be achieved through CEACAM6 silencing using CEACAM6-specific siRNA (Duxbury et al 2004f) or inhibition of CEACAM6 function using an antibody fragment can affect cell migration, cell invasion, and cell adhesion in vitro (Blumenthal et al, 2005). These observations strongly suggest that CEACAM6 is a good biomarker for various tumors. While anti-CEACAM6 antibodies may be candidates for development of antibody-based drugs against pancreatic and other cancers, one must tread carefully in the strategies targeting CEACAM6. Unlike antibodies such as Trastuzumab against HER2 which has direct effect in tumor progression (Baselga et al, 1999; Vogel et al, 2001), un-conjugated anti-CEACAM6 antibody may not have effect on tumor growth (Strickland et al, 2009) in an in vivo study. Specifically, the monoclonal antibody alone showed no effect on tumour progression, however the same antibody conjugated to an anti-cancer drug was able to limit the tumour development in mouse model.

Monoclonal antibodies against CEACAM6 are available, including anti-CEACAM6 monoclonal 13-1 (Riley et al, 2009), anti-CEACAM6 MAb (Strickland et al 2009), CEACAM6 monoclonal antibody (M02), clone 1G2 (Abnova), CEACAM6 Mouse anti-Human Monoclonal (5F7)

(Antibody LifeSpan Biosciences), Human CEACAM-6 MAb (Clone 439424) (R & D Systems). All of these antibodies are gamma immunoglobulins (IgG) and share common disadvantages of such molecules including difficulty in engineering, difficulty in production, and slow tissue penetration when used in vivo.

Thus, there remains a need in the art for antibodies that have high affinity but can overcome the shortcomings of IgGs and their variants. for the need for such antibodies is great in research, as reagents for in vitro or in vivo diagnostics, and in therapeutics for diseases associated with CEACAM6.

SUMMARY OF THE INVENTION

The present invention relates to anti-CEACAM6 antibodies and uses thereof. More specifically, the present invention is directed to anti-CEACAM6 antibodies and fragments thereof, and uses thereof.

The present invention provides isolated or purified antibodies or fragments thereof specific for CEACAM6, wherein the antibody or fragment thereof binds to an epitope comprising the sequence NRIGYSWYKG (SEQ ID NO:7).

The present invention further provides an isolated or purified antibody or fragment thereof, comprising
  a complementarity determining region (CDR) 1 comprising the sequence of GRTNSVYTMG (SEQ ID NO:1);
  a CDR2 comprising the sequence of IMWGAGTNTHYADSVKG (SEQ ID NO:2); and
  a CDR3 comprising the sequence of AANRGIPIAGRQYDY (SEQ ID NO:3),
wherein the antibody or fragment thereof is specific for CEACAM6. The isolated or purified antibody or fragment thereof as just described may be a single-domain antibody (sdAb). The sdAb may be of camelid origin. In one example, the isolated or purified antibody or fragment thereof may comprise the sequence:

```
                                          (SEQ ID NO: 4)
QVKLEESGGGLVQAGGSLRLSCRTSGRTNSVYTMGWFRQAPGKEREFVAQ

IMWGAGTNTHYADSVKGRFTISRDSAESTVYLQMNSLKPEDTAVYYCAAN

RGIPIAGRQYDYWGQGTQVTVSS,
``` or a sequence substantially identical thereto. The isolated or purified antibody or fragment thereof may bind to an epitope comprising the sequence NRIGYSWYKG (SEQ ID NO:7).

The isolated or purified antibodies or fragments thereof described herein may be in a multivalent display. For example, the isolated or purified antibodies or fragments thereof may be expressed linked to a Fc fragment; in one specific example, the Fc fragment may be the mouse Fc2b or human Fc1.

The present invention also provides a nucleic acid molecule encoding the isolated or purified antibodies or fragments thereof described above. Also encompassed by the present invention is a vector comprising the nucleic acid molecule just described.

The present invention further provides the isolated or purified antibodies or fragments thereof described herein immobilized onto a surface.

Additionally, the present invention provides the isolated or purified antibodies or fragments thereof linked to a cargo molecule. The cargo molecule may be any suitable diagnostic or therapeutic agent known in the art.

The present invention also provides a method of blocking CEACAM6 and decrease its invasiveness; of reducing cell proliferation, invasion, and MMP-9 activity; and of reducing the ability of tumor cells to promote angiogenesis. The method comprises administering 2A3, 2A3-Fc, or a combination thereof to a subject in need thereof.

The present invention further provides in vivo method of detecting tumors, comprising:
  a) administering the isolated or purified antibody or fragment thereof of the present invention linked to a diagnostic agent to a subject; and
  b) detecting the binding of the molecular imaging agent.

In the in vivo method as described above, the diagnostic agent may be radioisotope, a paramagnetic label, a fluorophore, a Near Infra-Red (NIR) fluorochrome or dye, an affinity label, or a detectable protein-based molecule via genetic fusion to the antibody. In the method as just described, the step of detecting (step b)) may be accomplished by any appropriate imaging method including, but not limited to non-invasive optical imaging, ultrasound, MRI, PET, or SPECT.

The present invention also provides an in vitro method of tumor diagnostics, comprising:
  a) contacting a tumor sample with the isolated or purified antibody or fragment thereof linked to a diagnostic agent; and
  b) detecting the binding of the isolated or purified antibody or fragment thereof.

In the in vitro method as described above, the diagnostic agent may be FITC or Enhanced Green Fluorescent Protein (EGFP) via genetic fusion to the antibody. In the method as just described, the step of detecting (step b)) may be accomplished by any appropriate method including, but not limited to fluorescence imaging.

As described herein, antibodies in the form of sdAb are presently described that are specific for CEACAM6. The sdAb against CEACAM6, which have an inhibitory effect on BxPC3 cell proliferation in an in vitro assay, are candidates for the development of antibody-based drugs against pancreatic and other cancers. In particular 2A3 and 2A3-Fc recognize a linear epitope, NRIGYSWYKG, on CEACAM6. Single-domain antibodies such as those identified presently are known to possess stability; they show ease in antibody engineering; and have superior tissue penetration ability due to their small size.

The sdAb 2A3 and 2A3-Fc blocked the CEACAM6 antigen and decreased its invasiveness. Treatment of BxPC3 tumor cells with 2A3 or 2A3-Fc reduced cell proliferation, invasion, and MMP-9 activity. Such treatment also reduced the ability of the conditioned media of pancreatic tumor cells to promote HUVEC cell angiogenesis. In contrast, gemcitabine only affected BxPC3 cell proliferation, did not affect MMP activity, and did not reduce HUVEC capillary-like structure formation. Thus, the 2A3 antibody can be a useful addition to gemcitabine in treating pancreatic cancer when gemcitabine alone would fails to inhibit angiogenesis.

An important advantage of these antibodies over drugs used for chemotherapy is that they are more specific for tumors that over-express CEACAM6 antigen. Therefore, this might result in reduced general cell toxicity and cancer cell chemo-resistance. The Fc-conjugate version (2A3-Fc) is also advantageous for its long half life in circulation, and its ability to induce antibody-dependent cellular cytotoxicity and complement-dependent cytotoxicity.

Additionally, anti-CEACAM6 antibodies (Abs) of different sizes (2A3, 2A3-Fc, and 9A6 Ab) were labelled with $^{64}$Cu to image CEACAM6 expression in xenografted pancreatic tumors and biodistribution of antibodies in vivo.

High expression of CEACAM6 on BxPC3 cells was confirmed by high fluorescence intensity on cell surface with FITC-Ab staining. All three antibodies showed strong CEACAM6 binding. Ex vivo immunostaining on tumor sections at 24 hr after Ab injection demonstrated specific tumor targeting of both 2A3-mFc and 9A6. $^{64}$Cu-DOTA-2A3 showed fast tumor uptake and rapid whole-body clearance. BxPC3 tumors were clearly visualized with $^{64}$Cu-DOTA-2A3mFc and $^{64}$Cu-DOTA-9A6 PET. At 24 hr p.i. of $^{64}$Cu-DOTA-2A3mFc and $^{64}$Cu-DOTA-9A6, the tumor uptake was 57.8±3.73 and 98.2±6.12% ID/g, respectively. Compared with the full length antibody 9A6, the heavy chain antibody 2A3-mFc showed higher tumor uptake, lower liver uptake and shorter circulation half-life. Conclusion: The heavy chain antibody 2A3-mFc is superior to the single domain antibody and the full length antibody with regard to tumor detection and pharmacokinetics. It has great potential to be developed for CEACAM6-targeted pancreatic cancer imaging and therapy.

The anti-CEACAM6 specific single domain antibody 2A3 and heavy chain antibody 2A3-Fc were compared to the commercially available mouse monoclonal antibody 9A6. The three CEACAM6 imaging probes were evaluated in a mouse model of human pancreatic cancer. All three antibodies showed positive tumor accumulation. Moreover, the tumor/non-tumor ratios were high enough to present a very clear tumor contrast. All the imaging data supported the feasibility of pancreatic cancer imaging by targeting CEACAM6. Especially, both 2A3-Fc and 9A6 showed high tumor/liver ratio, which facilitates primary pancreatic cancer detection in real scenario.

Due to its small molecular weight (16 kDa), the sdAb 2A3 exhibited fast clearance kinetics. The tumors were clearly visible as early as 30 min after tracer injection, with decent uptake of 4.22±1.13% ID/g. However, the tumors showed no apparent contrast to liver, which may inhibit tumor detection near this organ. One advantage of small sized antibodies is to perform imaging repetitively after labelling with short-half radioisotopes such as $^{68}$Ga ($t_{1/2}$=68 min) or $^{18}$F ($t_{1/2}$=108 min) (Han & Zhu, 2010), allowing sequential non-invasive imaging of the pharmacodynamics of the targeted drug. Kidneys showed extremely high radioactivity accumulation resulting from dominant rental-urinary excretion.

With weaker binding affinity and fast clearance, the absolute dose deposition was much lower for the sdAb, compared to the full length antibody. In the BxPC3 model, 9A6 showed gradually increasing tumor uptake with time. At 24 hr after injection, the tumor uptake reached 57.8±3.73% ID/g, which was higher than that from anti-EGFR or HER2 antibodies in EGFR or HER2 positive tumor models (Zhang et al, 2009a; 2009b). However, the tumor to blood ratio was only 3.61, owing to its long blood circulation time.

With bivalent binding, 2A3-Fc exhibited better tumor deposition than the single domain counterpart, yet cleared faster from circulation than the intact antibody because of its smaller molecular size. At 24 hr after injection, the BxPC3 tumors showed an extremely high accumulation of 2A3-Fc (98.2±6.12% ID/g), which was significantly higher than that of 9A6. The tumor/non-tumor ratios were also much higher than that of 9A6, especially tumor/blood ratio (9.25±1.64 vs. 3.61±0.28). As early as 8 hrs after tracer injection, the tumor showed apparent contrast to the liver. However, it is noteworthy that the high tumor uptake was also partially related to the tumor size, which was relatively small at imaging time (average of 184 mm$^3$). Roughly 18% of the total injected dose distributed to tumor region. With a molecular size around 80 kDa, 2A3-Fc still showed much less renal-urinary excretion compared with the single domain antibody 2A3.

In order to confirm the specificity of antibody distribution in the tumor region, PET imaging was also performed with a control antibody, murine IgG. The tumor showed radioactivity uptake of 8.33±1.06% ID/g, which was from non-specific perfusion of the antibody (Birkedal-Hansen et al, 2008). Based on the dramatic difference of tumor uptake between IgG and 9A6, it is reasonable to conclude that the high tumor uptake of 9A6 mainly resulted from specific targeting of the antibody to the antigen CEACAM6. Further investigations of the microscopic distribution of 9A6 and 2A3-Fc within BxPC3 tumors, it was found that 2A3-Fc showed more diffusive distribution than 9A6. Moreover, the cell membrane binding of both antibodies was clearly distinguished, which confirmed the specific binding of the antibodies (FIG. 6). However, 2A3-Fc did not achieve homogenous distribution within the tumor.

BRIEF DESCRIPTION OF THE DRAWINGS

These and other features of the invention will now be described by way of example, with reference to the appended drawings, wherein:

FIG. 1C shows the amino acid sequence of 2A3 (SEQ ID NO:4).

NRIGYSWYKGERVDG, SEQ ID NO:6) are stained positive by 2A3 in a CEACAM6 peptide array.

Figure 6A:
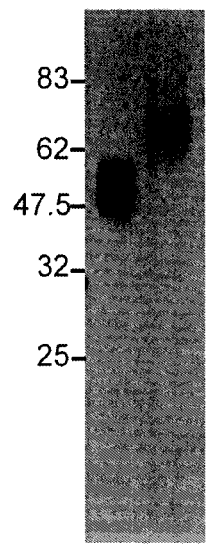
Figure 6B:
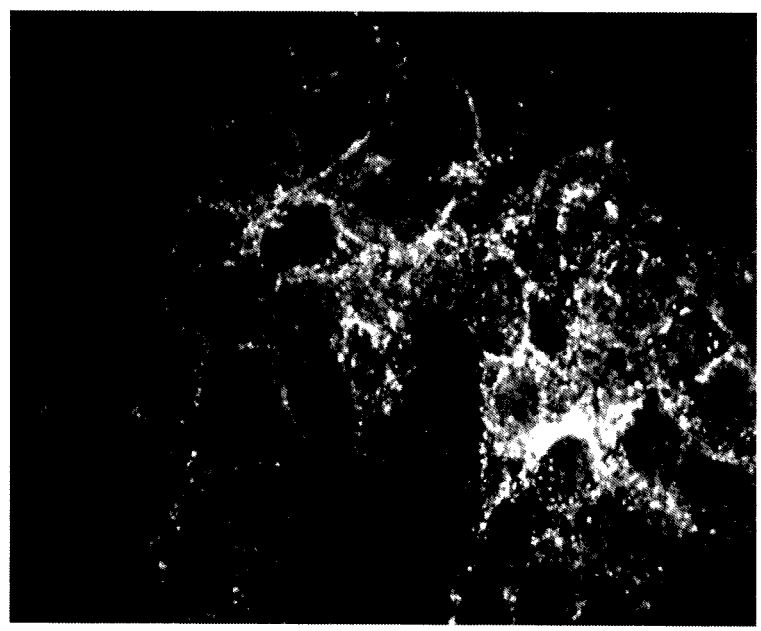
Figure 6C:
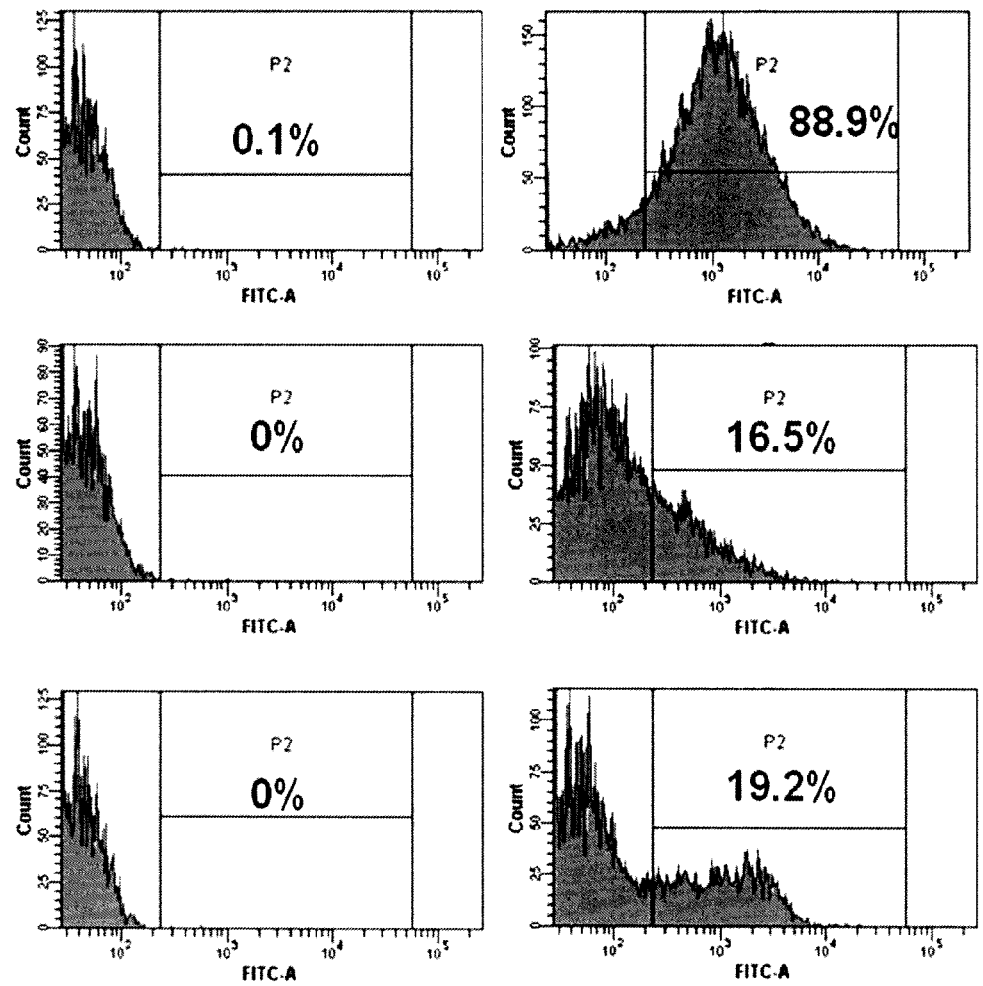

FIG. 6A shows a Western blot analysis of binding of 2A3 to mammalian cell expressed recombinant CEACAM6 (left panel) or CEACAM6 in BxPC3 cell lysates (right panel). Detection is carried out by using goat anti-llama antibody and then HRP-conjugated swine anti-goat antibody. Molecular markers (in kDa) are indicated. FIG. 6B shows BxPC3 cells stained with FITC-labelled 2A3 (green FITC staining presented as bright in the figure). The DAPI was used to stain the nucleus, and 2A3-FITC for staining of CEACAM6. FIG. 6C shows FACS analysis results of 2A3 binding to BxPC3, LS174T and A549 cells. The FITC-labelled 2A3 was incubated with fixed cells and were analyzed by FACS. 2A3 (right panel) and S20, a control antibody (left panel) both were used at 5 μg/ml concentration.

Figure 2:
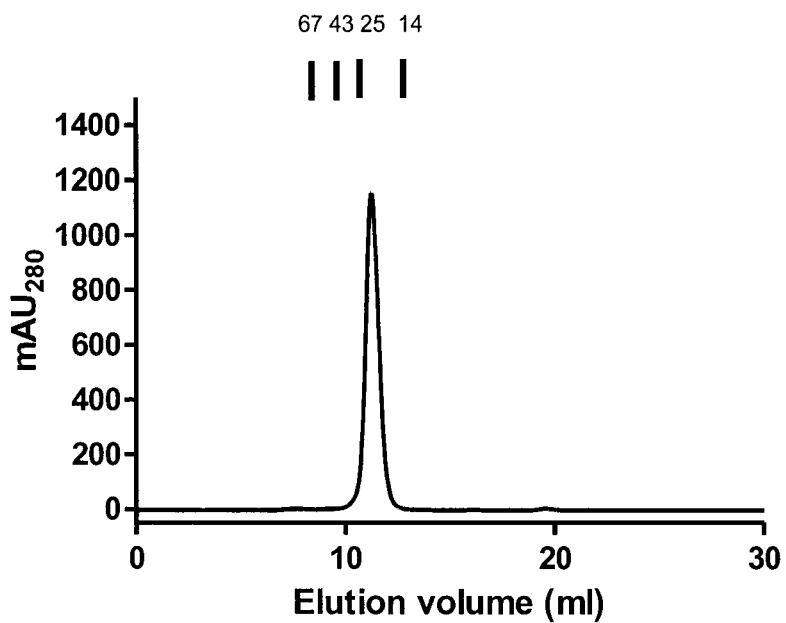
FIG. 2 shows a size exclusion chromatogram of IMAC purified 2A3 using a Superdex 75 column. Superdex separation was carried out in PBS. The size of molecular markers (in kDa) are indicated on the top.
Figure 3:
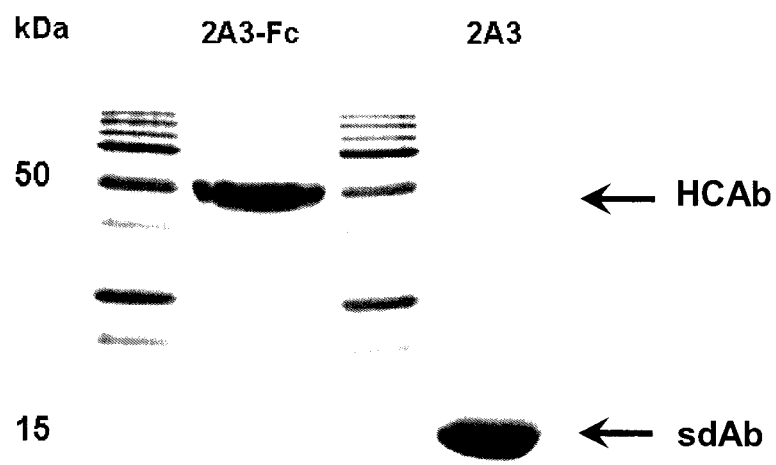
FIG. 3 shows a reducing SDS-PAGE gel of the purified 2A3 and 2A3-Fc antibodies. The recombinant 2A3-Fc is approximately half the size of a conventional IgG. The sdAb 2A3, and 2A3-Fc were expressed and purified to >95% purity (by SDS-PAGE).
Figure 7:
Figure 7:
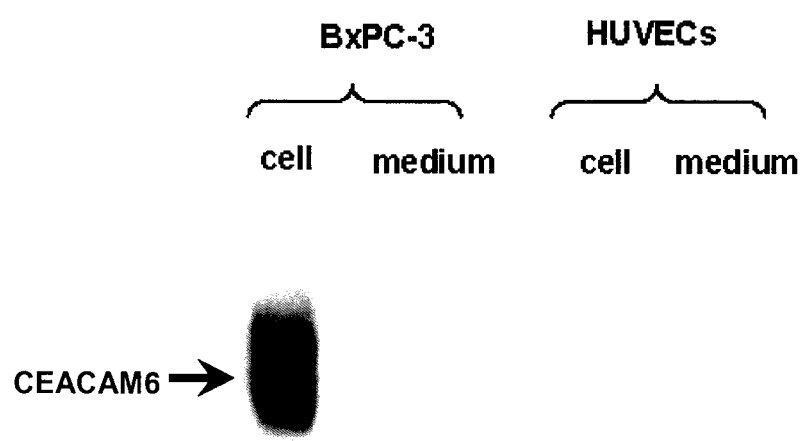

FIG. 7 shows the expression level of CEACAM6 by BxPC3 and HUVEC cells and in their conditioned media. In FIG. 7A, 2A3-Fc antibody was conjugated with Alexa Fluor 594 for immunocytochemistry to visualize CEACAM6 expression on BxPC3 cell surface (right). An isotype control VTI1-Fc was used as a negative control (left). DAPI was used as nuclear stain. Whereas 2A3-Fc stained the BxPC3 positively, the control antibody VTI1-Fc did not stain the cells. FIG. 7B shows a Western blot to detect CEACAM6 in BxPC3 and HUVEC cells. While BxPC3 cells showed very high levels of CEACAM6 expression, no CEACAM6 was detected in the culture medium, or in HUVEC cells.

Figure 8A:
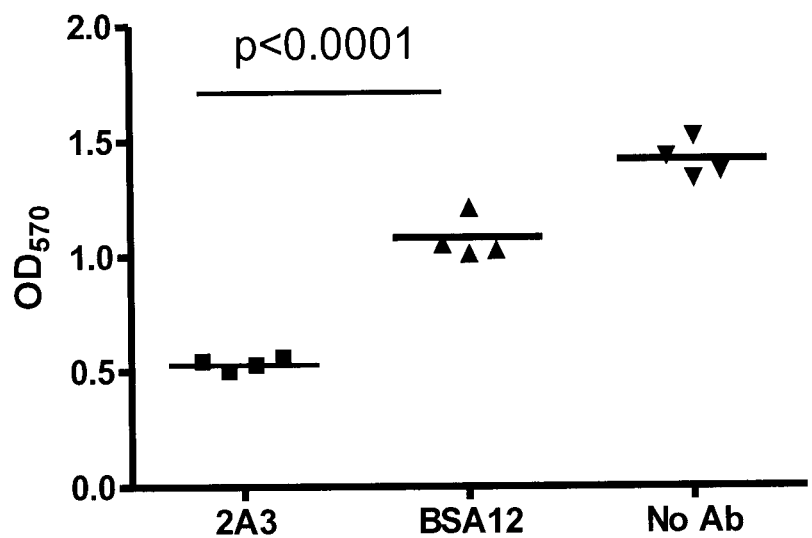
Figure 8B:
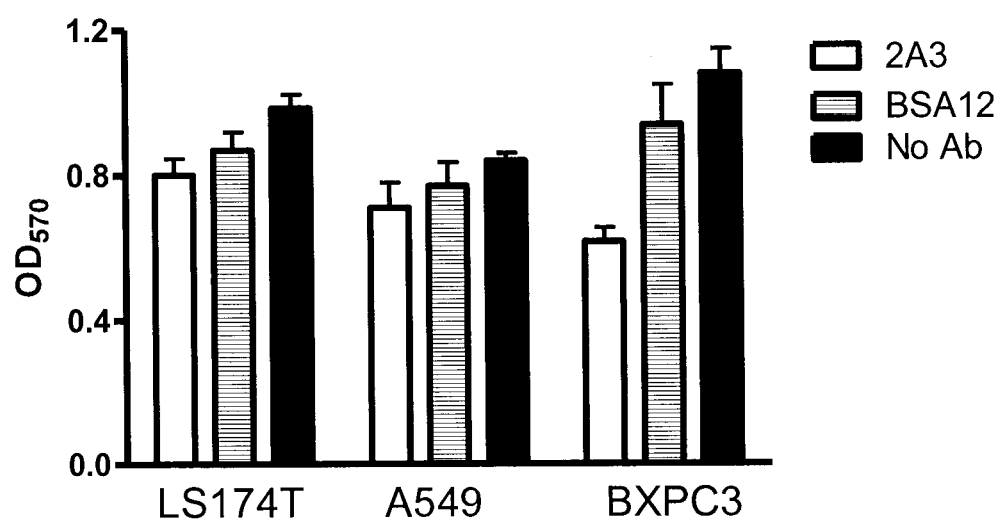

FIG. 8A shows the BxPC3 cell proliferation inhibition by 2A3 as measured by MTT assay. Cells were cultured with the sdAb (2A3), control sdAb (BSA12) or without any antibody (no Ab) for 5 days in quadruplicate. FIG. 8B is a bar graph displaying cell proliferation results for LS174T, A549 and BxPC3 cells as measured by MTT assay.

Figure 9:
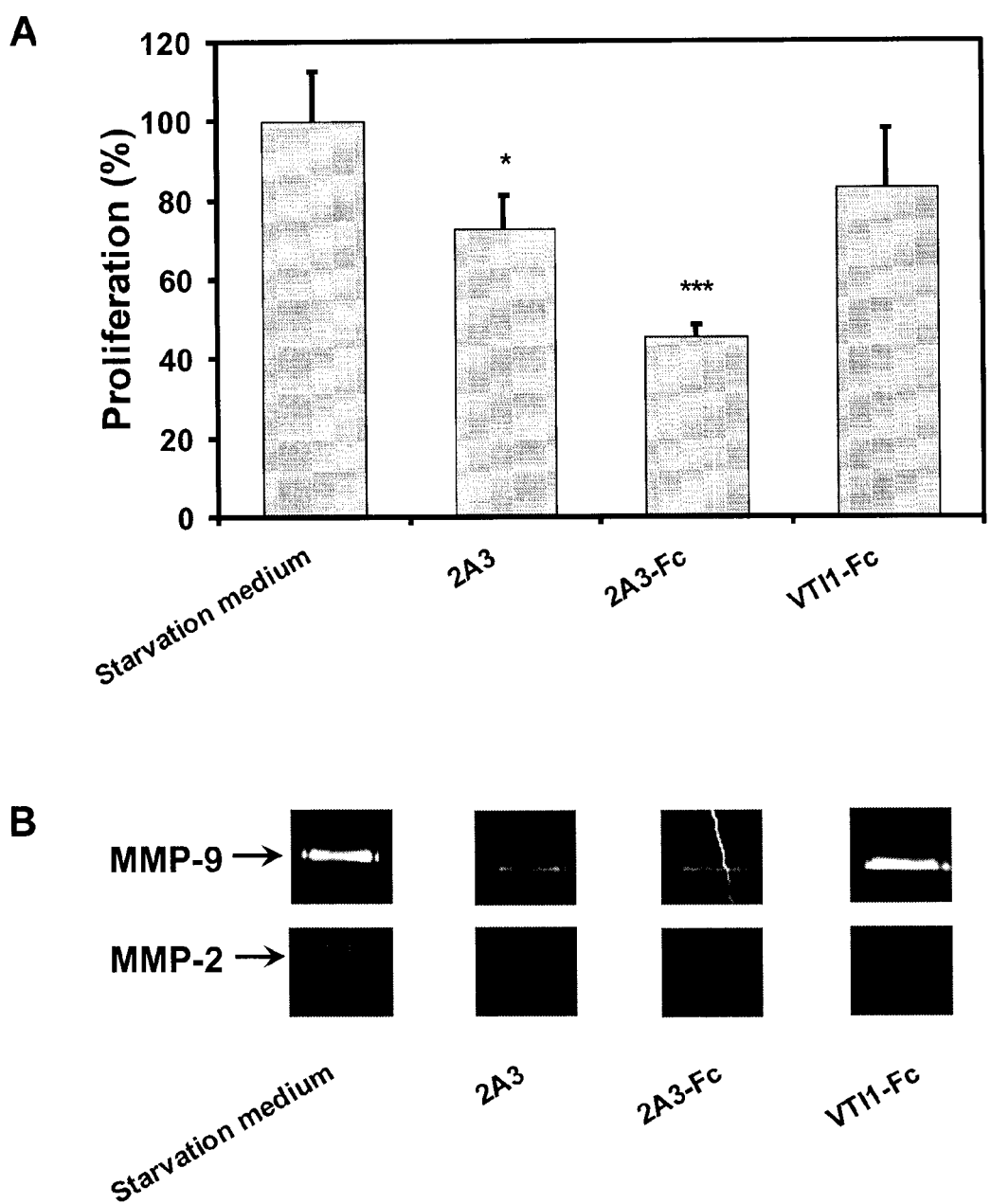

FIG. 9 shows results of inhibition of BxPC3 cell proliferation and MMP9 and MMP2 activities by the antibodies. FIG. 9A shows results of MTT assays for 2A3 and 2A3-Fc anti-CEACAM6 antibodies to determine their effect on BxPC3 cells proliferation; VTI1-Fc, an isotype control antibody that does not bind to CEACAM6, was used as a negative control. FIG. 9B shows results of gelatin zymography to evaluate MMP-9 and MMP-2 activities. The 2A3 and 2A3-Fc antibodies showed significant reduction in MMP-9 activity in the media from BxPC3 cells.

Figure 10:
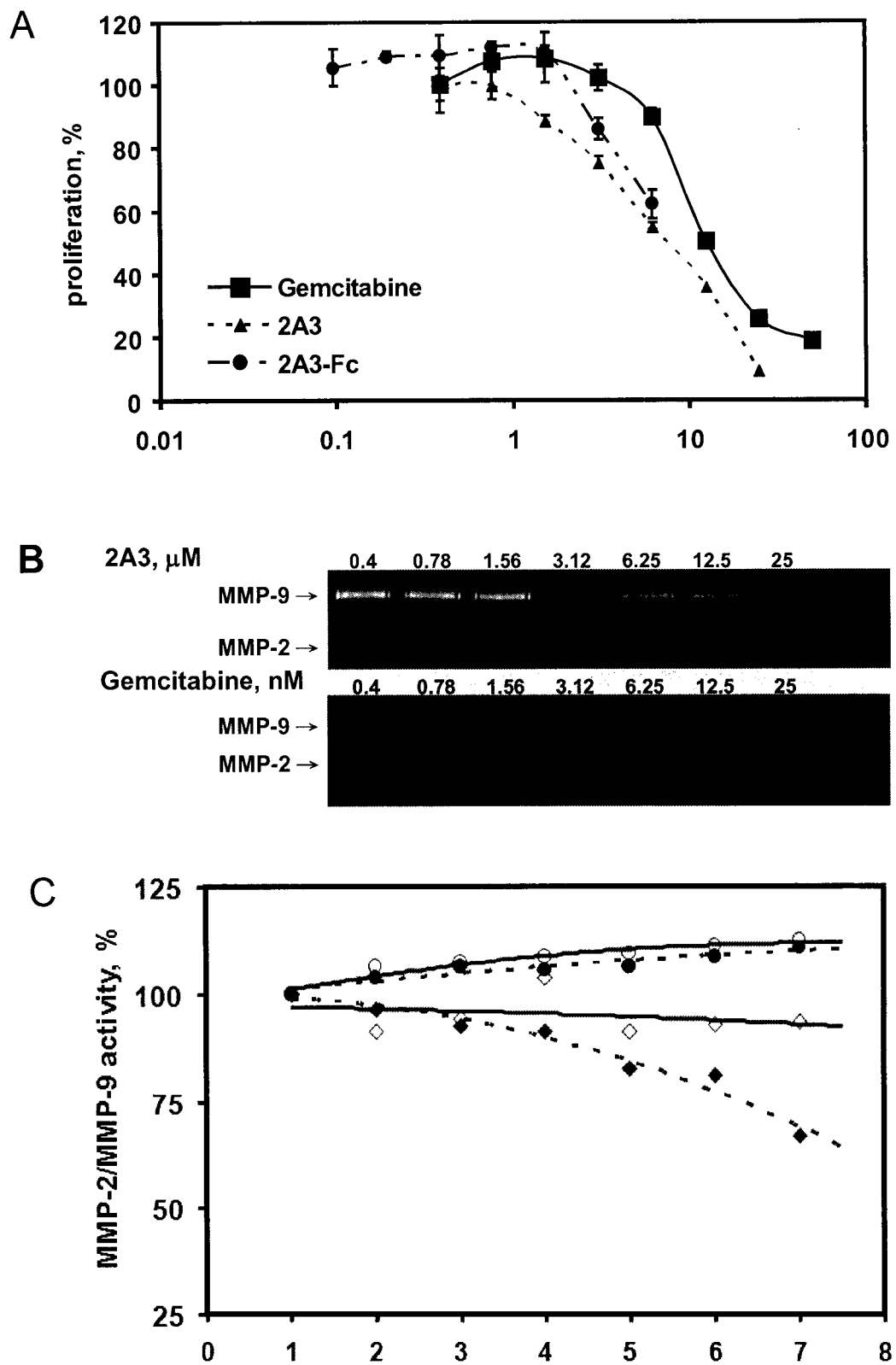

FIG. 10 shows the results of the in vitro proliferation and gelatinase activity assays. FIG. 10A is a graph depicting the percentage of proliferating BxPC3 cells after treatment with various amounts of 2A3, 2A3-Fc, or gemcitabine for 72 h (n=5); cell proliferation in starvation medium was used as control. The $IC_{50}$ for 2A3, 2A3-Fc, and gemcitabine were calculated as 6.5 μM, 8 μM, and 12 nM, respectively. FIG. 10B shows results of gelatin zymography to examine MMP-2 and MMP-9 activities. 2A3/2A3Fc, but not gemcitabine, inhibited MMP-9 activity. MMP-2 activity was not affected by the treatment. FIG. 10C is a graph showing the scale of MMP-9 activity reduction caused by 2A3/2A3-Fc treatment. 2A3-MMP-9 activity, filled diamonds; 2A3-MMP-2 activity, open diamonds; gemcitabine-MMP-9 activity, filled circles; gemcitabine-MMP-2 activity, open circles.

Figure 11:
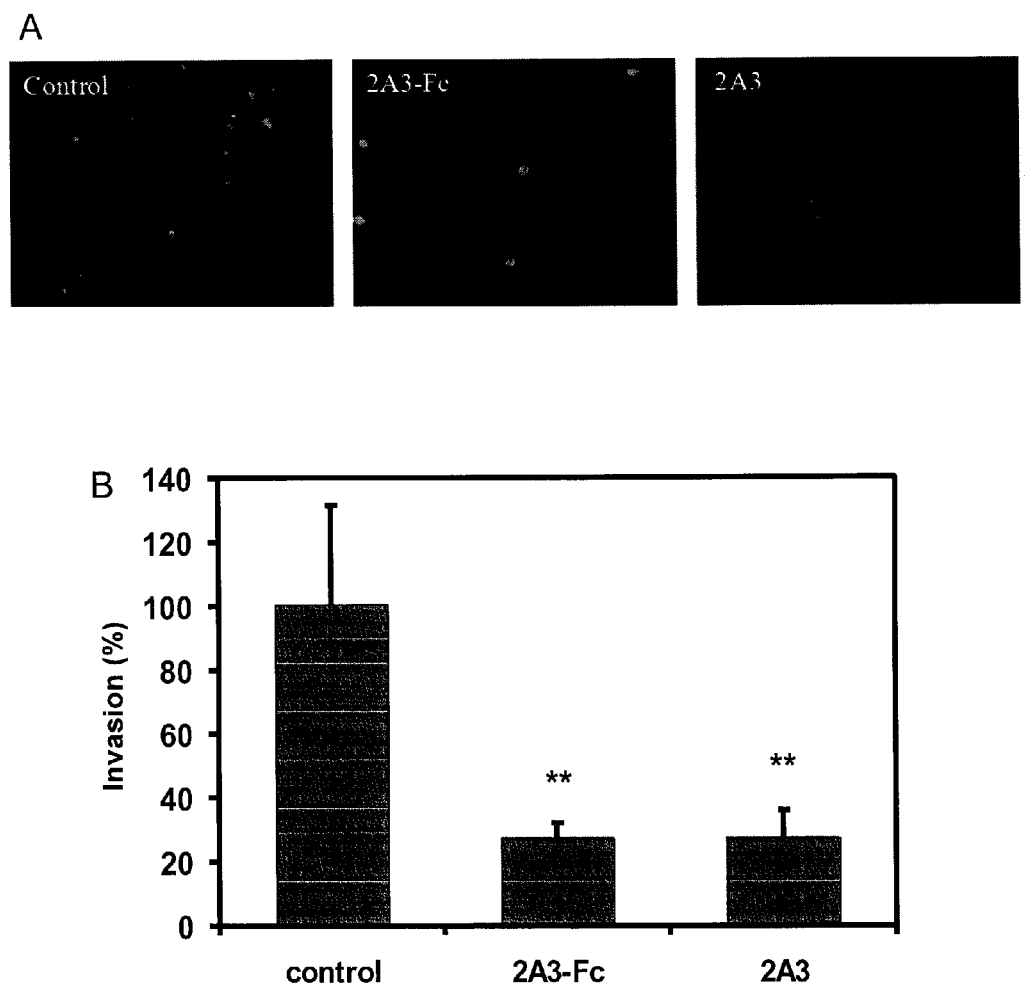

FIG. 11A shows the inhibition of BxPC3 invasion activity by 2A3/2A3-Fc-treatment. Cells from three random selected fields were counted and normalized against a starvation medium control. Both 2A3 and 2A3-Fc reduced the invasion activity of BxPC3. The invasive cells on the bottom surface were stained with Calcein AM and photos were taken at 100× magnification. FIG. 11B is a bar graph showing the scale of the reduction of BxPC3 cells by 2A3 and 2A3-Fc. The invasive cells on the bottom surface were stained with Calcein AM and counted by fluorescence microscopy. All experiments were performed in triplicate. **P<0.01

FIG. 12A shows inhibition of tubule formation in HUVEC cells treated with conditioned media from BxPC3 cells treated with 2A3 or 2A3-Fc. Both 2A3 and 2A3-Fc reduced tube formation by BxPC3 cells. Three fields that were randomly chosen were captured and the length of the capillary in each field was measured. P<0.01 in 2A3 and *P<0.001 in 2A3-Fc. FIG. 12B is a bar graph showing the scale of the inhibition of capillary-like tube formation (angiogenesis) by 2A3 or 2A3-Fc. sdAb 2A3 inhibited tubule formation by 21% and 2A3-Fc inhibited tubule formation by 49%.

Figure 13:
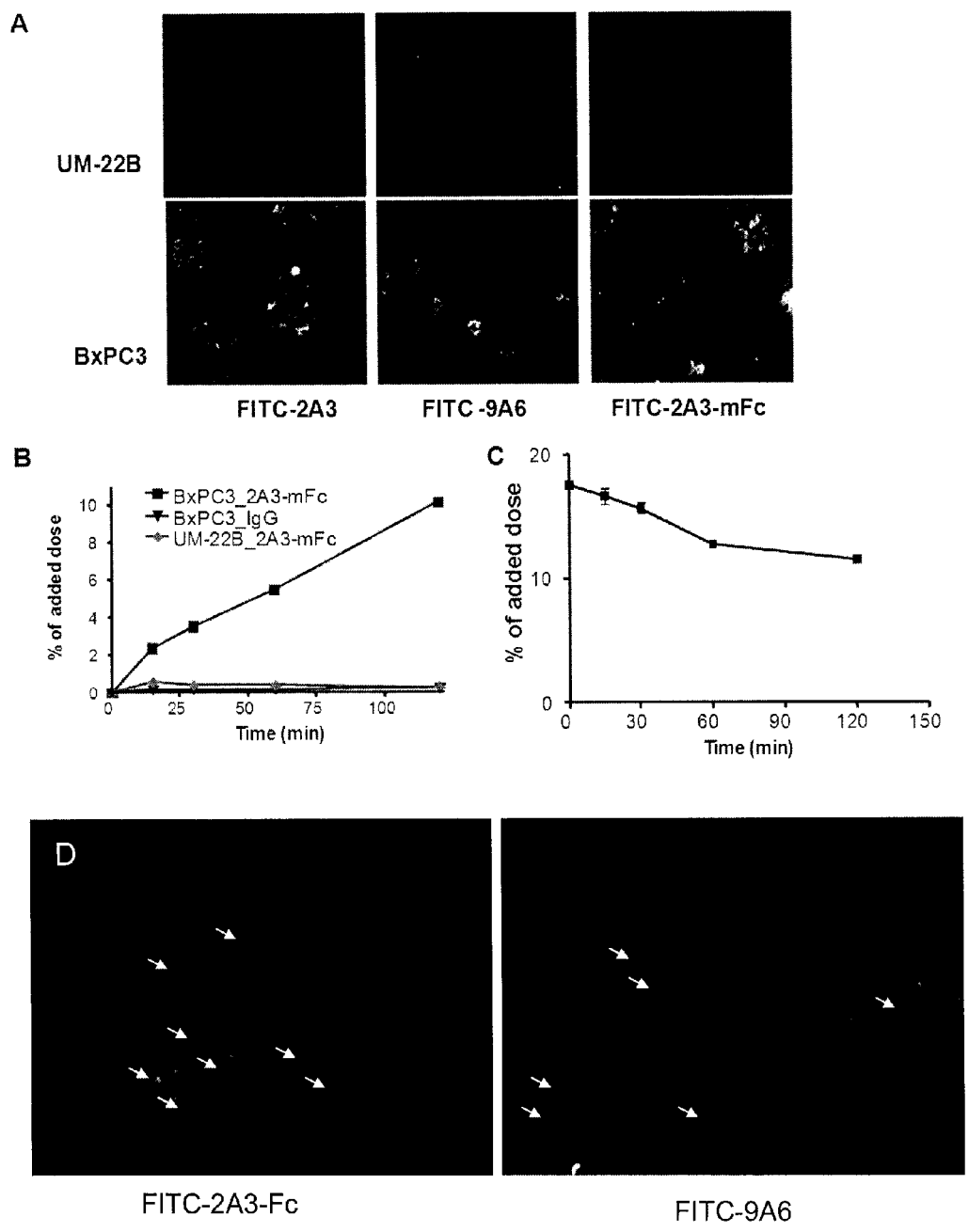

FIG. 13A shows results of in vitro immunostaining of CEACAM6-negative UM-SCC-22B and CEACAM6-positive BxPC3 cells. Results of cell uptake (FIG. 13B) and efflux (FIG. 13C) assays of $^{64}$Cu-DOTA-2A3-Fc and $^{64}$Cu-DOTA-IgG on BxPC3 or UM-SCC-22B cells are shown. The cell uptake and efflux was expressed as percentage of decay-corrected total input radioactivity. Data were from 2 experiments with triplicate samples and are expressed as mean±SD. FIG. 13D shows BxPC3 tumor sections stained in vitro with FITC-labelled anti-CEACAM6 antibodies to show cells retained CEACAM6 expression after growth in mice. Arrow (↘) indicate localization of fluorescence.

Figure 14:
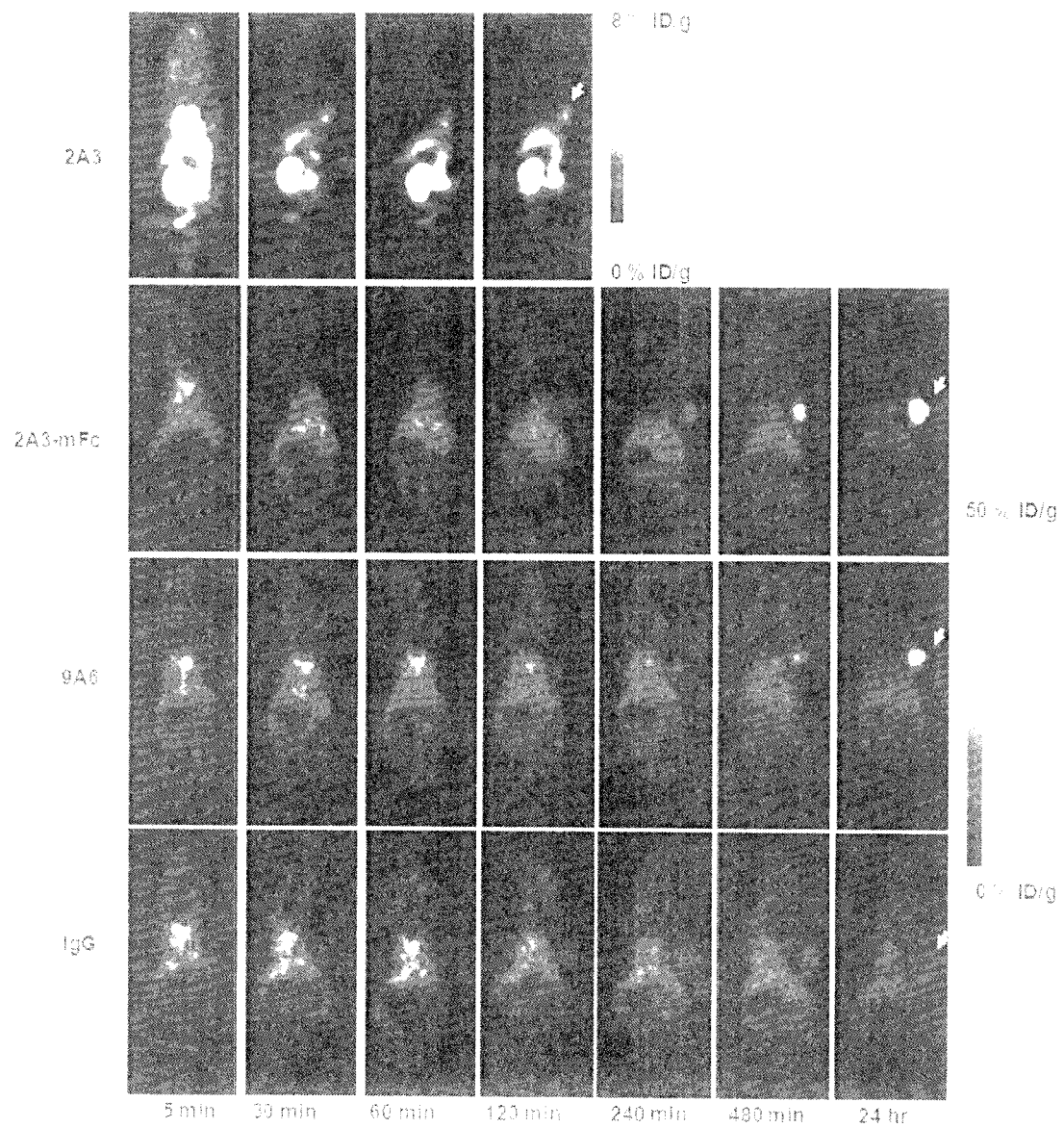

FIG. 14 shows microPET whole body images (coronal plane) of BxPC3 tumor bearing mice at different time points after tail vein injection of 3.7 MBq of 64Cu-DOTA-2A3, 64Cu-DOTA-2A3-mFc, 64Cu-DOTA-9A6 and 64Cu-DOTA-IgG. Tumors are indicated by white arrows at the last time point. The displayed plane was selected to best show the tumor cross section.

Figure 15:
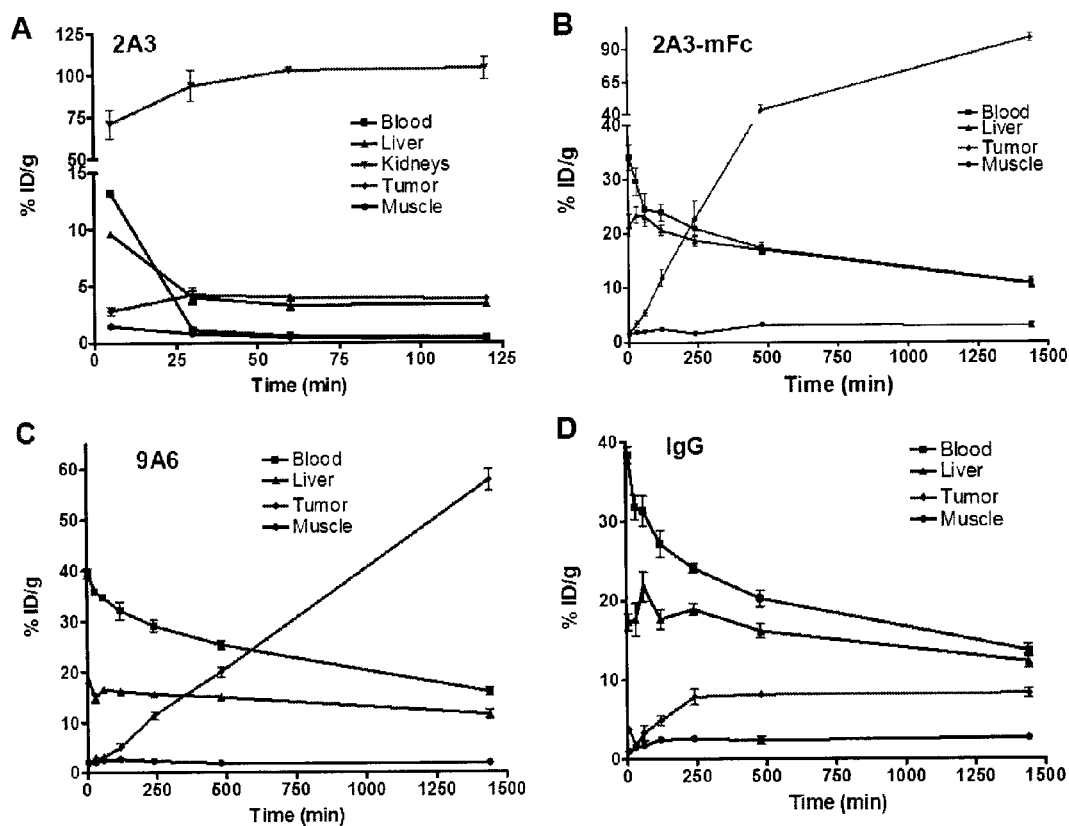

FIG. 15 shows uptake values for 2A3 (FIG. 15A), 2A3-mFc (FIG. 15B), 9A6 (FIG. 15C) and an IgG (FIG. 15D) at different points after tracer injection in the kidneys, liver, muscle, and BxPC3 tumor quantified from the region of interest (ROI) analysis on microPET scans (n=4).

Figure 16:
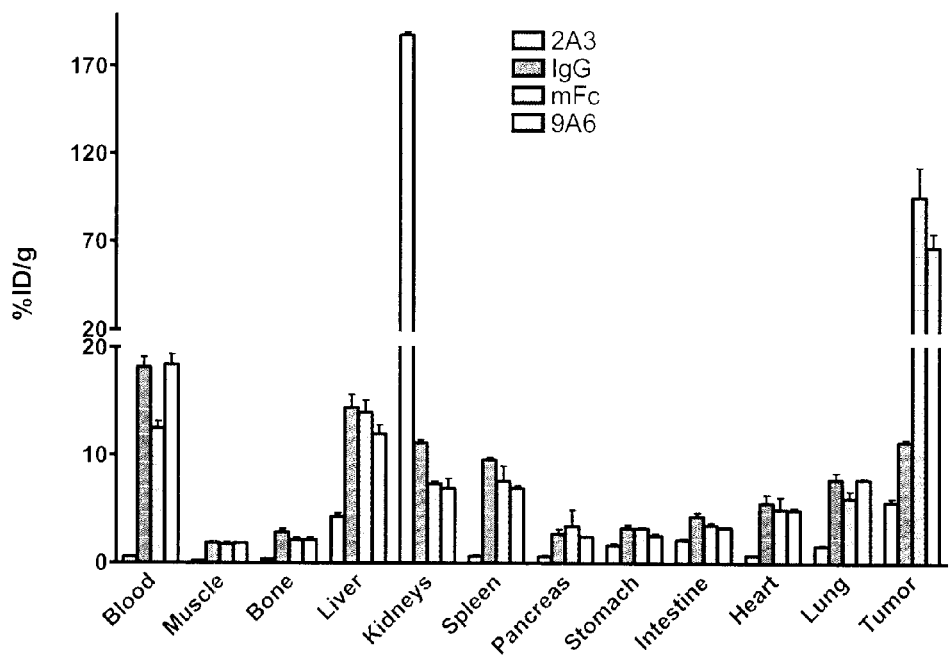

FIG. 16 is a bar graph indicating the biodistribution of 18F-FBEM-EM3106B in BxPC3 tumor bearing athymic nude mice after microPET imaging at the 2 h time point (2A3; n=4) or 24 h time point (2A3-Fc, 9A6 and IgG; n=4).

Figure 17:
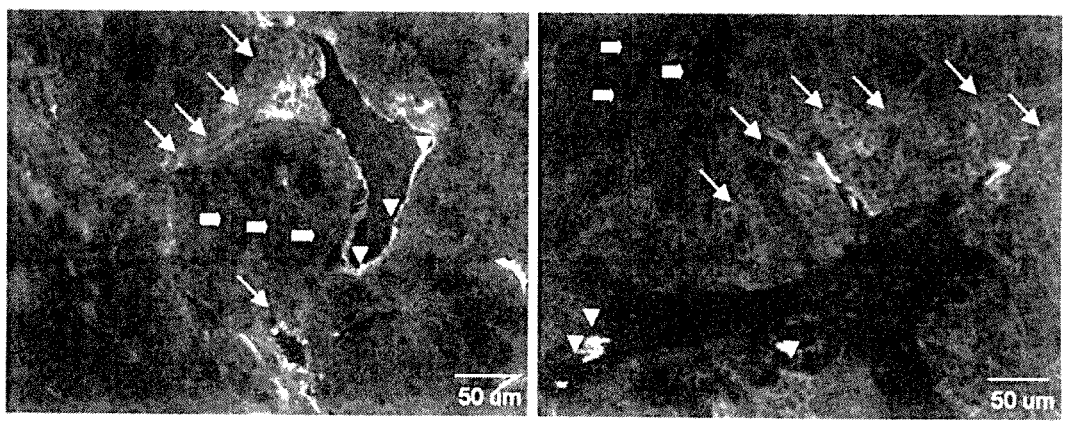

FIG. 17 shows images of tumor sections stained with Cy3-conjugated donkey anti-mouse human IgG. The sections also were co-stained with CD31 for tumor vasculature visualization (▼ Dylight 488 for CD31; ↘ Cy3 for CEACAM6; ⇒ DAPI for nuclei visualization).

DETAILED DESCRIPTION OF THE INVENTION

The present invention relates to anti-CEACAM6 antibodies and uses thereof. More specifically, the present invention is directed to anti-CEACAM6 antibodies and fragments thereof, and uses thereof.

The present invention provides isolated or purified antibodies or fragments thereof specific for CEACAM6, wherein the antibody or fragment thereof binds to an epitope comprising the sequence NRIGYSWYKG (SEQ ID NO:7).

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important immunological events. The variable region of an antibody contains the antigen binding determinants of the molecule, and thus determines the specificity of an antibody for its target antigen. The majority of sequence variability occurs in six hypervariable regions, three each per variable heavy and light chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen. Various schemes exist for identification of the regions of hypervariability, the two most common being those of Kabat and of Chothia and Lesk. Kabat et al (1991a; 1991b) define the "complementarity-determining regions" (CDR) based on sequence variability at the antigen-binding regions of the VH and VL domains. Chothia and Lesk (1987) define the "hypervariable loops" (H or L) based on the location of the structural loop regions in the VH and VL domains. As these individual schemes define CDR and hypervariable loop regions that are adjacent or overlapping, those of skill in the antibody art often utilize the terms "CDR" and "hypervariable loop" interchangeably, and they may be so used herein. For this reason, the regions forming the antigen-binding site are referred to as CDR L1, CDR L2, CDR L3, CDR H1, CDR H2, CDR H3 in the case of antibodies comprising a VH and a VL domain; or as CDR1, CDR2, CDR3 in the case of the antigen-binding regions of either a heavy chain or a light chain. The CDR/loops are referred to herein according to the IMGT numbering system (Lefranc et al., 2003), which was developed to facilitate comparison of variable domains. In this system, conserved amino acids (such as Cys23, Trp41, Cys 104, Phe/Trp 118, and a hydrophobic residue at position 89) always have the same position. Additionally, a standardized delimitation of the framework regions (FR1: positions 1 to 26; FR2: 39 to 55; FR3: 66 to 104; and FR4: 118 to 128) and of the CDR (CDR1: 27 to 38, CDR2: 56 to 65; and CDR3: 105 to 117) is provided.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fab, F(ab')$_2$, single domain antibody (sdAb; a fragment composed of a single $V_L$ or $V_H$), and multivalent presentations of any of these.

In a non-limiting example, the antibody fragment may be an sdAb derived from naturally-occurring sources. Heavy chain antibodies of camelid origin (Hamers-Casterman et al, 1993) lack light chains and thus their antigen binding sites consist of one domain, termed $V_HH$. sdAb have also been observed in shark and are termed $V_{NAR}$ (Nuttall et al, 2003). Other sdAb may be engineered based on human Ig heavy and light chain sequences (Jespers et al, 2004; To et al, 2005). As used herein, the term "sdAb" includes those sdAb directly isolated from $V_H$, $V_HH$, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, e.g., camelization, or other methods of antibody engineering. Also encompassed by the present invention are homologues, derivatives, or fragments that retain the antigen-binding function and specificity of the sdAb.

SdAbs are excellent building blocks for novel antibody molecules due to their high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996).

A person of skill in the art would be well-acquainted with the structure of a single-domain antibody (see, for example, 3DWT, 2P42 in Protein Data Bank). A sdAb comprises a single immunoglobulin domain that retains the immunoglobulin fold; most notably, only three CDR form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3, and numbered as defined by Kabat et al (1991b).

The antibody or fragment thereof of the present invention is specific for carcinoembryonic antigen related cell adhesion molecule 6 (CEACAM6). CEACAM6 is also known in the art as non-specific cross-reacting antigen (NCA) or CD66c. While CEACAM6 has been observed in normal human tissues (Buchegger et al, 1984), its expression is elevated in many solid tumors such as breast, pancreatic, ovarian, lung and colon cancer (Blumenthal et al, 2007). The sequence of CEACAM6 may be, but is not limited to:

```
                                            (SEQ ID NO: 8)
MGPPSAPPCRLHVPWKEVLLTASLLTFWNPPTTAKLTIESTPFNVAEGKE

VLLLAHNLPQNRIGYSWYKGERVDGNSLIVGYVIGTQQATPGPAYSGRET

IYPNASLLIQNVTQNDTGFYTLQVIKSDLVNEEATGQFHVYPELPKPSIS

SNNSNPVEDKDAVAFTCEPEVQNTTYLWWVNGQSLPVSPRLQLSNGNMTL

TLLSVKRNDAGSYECEIQNPASANRSDPVTLNVLYGPDGPTISPSKANYR

PGENLNLSCHAASNPPAQYSWFINGTFQQSTQELFIPNITVNNSGSYMCQ

AHNSATGLNRTTVTMITVSGSAPVLSAVATVGITIGVLARVALI,
``` or a sequence substantially identical thereto.

The present invention further provides an isolated or purified antibody or fragment thereof, comprising
    a complementarity determining region (CDR) 1 comprising the sequence of GRTNSVYTMG (SEQ ID NO:1);
    a CDR2 comprising the sequence of IMWGAGTNTHY-ADSVKG (SEQ ID NO:2); and
    a CDR3 comprising the sequence of AANRGIP-IAGRQYDY (SEQ ID NO:3),
wherein the antibody or fragment thereof is specific for CEACAM6. The antibody as just described may recognize and bind to an epitope comprising the sequence NRIGYSW-YKG (SEQ ID NO:7).

The terms "antibody" and "antibody fragment" ("fragment thereof") are as defined above. As previously stated, the antibody or fragment thereof may be an sdAb. The sdAb may be of camelid origin or derived from a camelid $V_HH$, and thus may be based on camelid framework regions; alternatively, the CDR described above may be grafted onto $V_{NAR}$, $V_HH$ or $V_L$ framework regions. In yet another alternative, the hypervariable loops described above may be grafted onto the framework regions of other types of antibody fragments (Fv, scFv, Fab). The present embodiment further encompasses an antibody fragment that is "humanized" using any suitable method know in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the heavy chain CDR defined herein may be fused or grafted to a human variable region ($V_H$, or $V_L$), or to other human antibody fragment framework regions (Fv, scFv, Fab). In such a case, the conformation of said one or more than one hypervariable loop is preserved, and the affinity and specificity of the sdAb for its target (i.e., toxins A and B) is also preserved. CDR grafting is known in the art and is described in at least the following: U.S. Pat. No. 6,180,370, U.S. Pat. No. 5,693,761, U.S. Pat. No. 6,054,297, U.S. Pat. No. 5,859, 205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. No. 5,869,619, U.S. Pat. No. 5,766,886, U.S. Pat. No. 5,821,123, and European Patent No. 519596. Persons of skill in the art would be amply familiar with methods of preparing such humanized antibody fragments.

In a specific, non-limiting example, the antibody or fragment thereof may comprise the sequence:

(SEQ ID NO: 4)
QVKLEESGGGLVQAGGSLRLSCRTSGRTNSVYTMGWFRQAPGKEREFVAQ

IMWGAGTNTHYADSVKGRFTISRDSAESTVYLQMNSLKPEDTAVYYCAAN

RGIPIAGRQYDYWGQGTQVTVSS, or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 85% identical; in another example, the substantially identical sequences may be at least 70, 75, 80, 85, 90, 95, 96, 97, 98, 99, or 100% (or any percentage therebetween) identical at the amino acid level to sequences described herein. Importantly, the substantially identical sequences retain the activity and specificity of the reference sequence. In a non-limiting embodiment, the difference in sequence identity may be due to conservative amino acid mutation(s).

The antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection tag (for example, but not limited to c-Myc), a purification tag (for example, but not limited to a $His_5$ or $His_6$), or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags.

The antibody or fragment thereof of the present invention may also be in a multivalent display. Multimerization may be achieved by any suitable method of know in the art. For example, and without wishing to be limiting in any manner, multimerization may be achieved using self-assembly molecules as described in Zhang et al (2004a; 2004b) and WO2003/046560. The described method produces pentabodies by expressing a fusion protein comprising the antibody or fragment thereof of the present invention and the pentamerization domain of the B-subunit of an $AB_5$ toxin family (Merritt & Hol, 1995); the pentamerization domain assembles into a pentamer, through which a multivalent display of the antibody or fragment thereof is formed. Additionally, the pentamerization domain may be linked to the antibody or antibody fragment using a linker; such a linker should be of sufficient length and appropriate composition to provide flexible attachment of the two molecules, but should not hamper the antigen-binding properties of the antibody.

Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielson et al, 2000), c-jun/Fos interaction (de Kruif & Logtenberg, 1996), "Knob into holes" interaction (Ridgway et al, 1996).

Another method known in the art for multimerization is to dimerize the antibody or fragment thereof using an Fc domain. When applied in vivo, sdAbs are cleared quickly from the circulation (Bell et al., 2010). To solve this problem and to give sdAbs the ability to induce immune response after antigen binding, sdAbs may be fused to human Fc to generate chimeric heavy chain antibodies (Bell et al. Cancer Letters, 2010). In this approach, the Fc gene in inserted into a vector along with the sdAb gene to generate a sdAb-Fc fusion protein (Bell et al, 2010; Iqbal et al, 2010); the fusion protein is recombinantly expressed then purified. Such antibodies are easy to engineer and to produce (Zhang et al, 2009b), can greatly extend the serum half life of sdAbs, and may be excellent tumor imaging reagents (Bell et al., Cancer Letters, 2010).

The Fc domain in the multimeric complex as just described may be any suitable Fc fragment known in the art. The Fc fragment may be from any suitable source; for example, the Fc may be of mouse or human origin. In a specific, non-limiting example, the Fc may be the mouse Fc2b fragment or human Fc1 fragment (Bell et al, 2010; Iqbal et al, 2010).

The present invention also encompasses nucleic acid sequences encoding the molecules as described herein. The nucleic acid sequence may be codon-optimized for expression in various micro-organisms. The present invention also encompasses vectors comprising the nucleic acids as just described. Furthermore, the invention encompasses cells comprising the nucleic acid and/or vector as described.

The present invention further encompasses the isolated or purified antibody or fragments thereof immobilized onto a surface using various methodologies; for example, and without wishing to be limiting, the antibody or fragment may be linked or coupled to the surface via His-tag coupling, biotin binding, covalent binding, adsorption, and the like. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, a film, or any other useful surface.

The present invention further provides an antibody or fragment thereof linked to a cargo molecule; the antibody or fragment thereof may deliver the cargo molecule to a desired site. The cargo molecule may be any type of molecule that may diagnose or reduce/inhibit the growth of tumours. Thus, the cargo molecule may be linked to a therapeutic or diagnostic agent.

For example, and without wishing to be limiting in any manner, the therapeutic agent may be a radioisotope, which may be used for radioimmunotherapy; a toxin, such as an immunotoxin; a cytokine, such as an immunocytokine; a cytotoxin; an apoptosis inducer; an enzyme; or any other suitable therapeutic molecule known in the art. In the alternative, a diagnostic agent may include, but is by no means limited to a radioisotope, a paramagnetic label such as gadolinium or iron oxide, a fluorophore, a Near Infra-Red (NIR) fluorochrome or dye (such as Cy3, Cy5.5, Alexa680, Dylight680, or Dylight800), an affinity label (for example biotin, avidin, etc), fused to a detectable protein-based molecule, or any other suitable agent that may be detected by imaging methods. In a specific, non-limiting example, the antibody or fragment thereof may be linked to a fluorescent agent such as FITC or may genetically be fused to the Enhanced Green Fluorescent Protein (EGFP).

The antibodies of the present invention linked to a diagnostic agent, also referred to herein as a molecular imaging agent, may be used to perform diagnostic imaging. The imaging technique may include whole body imaging for diagnostic purposes or local imaging at specific sites, such as but not limited to sites of tumor growth, in a quantitative manner to assess the progression of disease or host response to a treatment regimen. The imaging may be accomplished by in vitro or in vivo by any suitable method known in the art. For example, and without wishing to be limiting, the diagnostic imaging technique may include immunohistochemistry, immunofluorescence staining, or a non-invasive (molecular) diagnostic imaging technology including, but not limited to:

Optical imaging;

Positron emission tomography (PET), wherein the detectable agent is an isotopes such as $^{11}C$, $^{13}N$, $^{15}O$, $^{18}F$, $^{64}Cu$, $^{62}Cu$, $^{124}I$, $^{76}Br$, $^{82}Rb$ and $^{68}Ga$, with $^{18}F$ being the most clinically utilized;

Single photon emission computed tomography (SPECT), wherein the detectable agent is a radiotracer such as $^{99m}Tc$, $^{111}In$, $^{123}I$, $^{201}Tl$, $^{133}Xe$, depending on the specific application;

Magnetic resonance imaging (MRI), wherein the detectable agent may be, for example and not limited to gadolinium, iron oxide nanoparticles and carbon-coated iron-cobalt nanoparticles thereby increasing the sensitivity of MRI for the detection of plaques.

The antibody or fragment thereof may be linked to the cargo molecule using any method known in the art (recombinant technology, chemical conjugation, chelation, etc.).

The present invention also provides an in vivo method of detecting tumors, comprising:

a) administering to a subject the antibody or fragment thereof described herein linked to a diagnostic agent; and b) detecting the binding of the antibody or fragment thereof.

In the in vivo method as described above, the diagnostic agent may be radioisotope, a paramagnetic label, a fluorophore, a Near Infra-Red (NIR) fluorochrome or dye, an affinity label, or a detectable protein-based molecule via genetic fusion to the antibody, or other suitable agent as described above. In the method as just described, the step of detecting (step b)) may be accomplished by any appropriate imaging method including, but not limited to non-invasive optical imaging, ultrasound, MRI, PET, or SPECT, or other suitable method. In the method as described above, the detection of localized antibody/molecular imaging agent accumulation indicates the presence and location of a tumor in the subject.

The present invention further provides an in vitro method of tumor diagnostics, comprising:
a) contacting a tumor sample with the isolated or purified antibody or fragment thereof linked to a diagnostic agent, as described herein; and
b) detecting the binding of the isolated or purified antibody or fragment thereof.

In the in vitro method as described above, the diagnostic agent may be a fluorescent dye or an enzyme; for example and without wishing to be limiting in any manner, the diagnostic agent may be FITC or may be a genetic fusion of the isolated or purified antibody or fragment thereof with Enhanced Green Fluorescent Protein (EGFP). In the method as just described, the step of detecting (step b)) may be accomplished by fluorescence imaging, immunohistochemistry, or other suitable method.

In the in vitro method as described above, the detection of localized antibody/molecular imaging agent accumulation indicates that the tumor expresses CEACAM6. For example and without wishing to be limiting in any manner, once a tumor is confirmed to express CEACAM6, anti-CEACAM6 therapies (such as those described herein) may be used to treat the subject.

The present invention also provides a method of blocking CEACAM6 and decrease its invasiveness; of reducing cell proliferation, invasion, and MMP-9 activity; and of reducing the ability of tumor cells to promote angiogenesis. The method comprises administering 2A3, 2A3-Fc, or a combination thereof to a subject in need thereof.

The sdAbs against CEACAM6 are candidates for the development of antibody-based drugs against pancreatic and other cancers. The sdAb 2A3 and 2A3-Fc can block the CEACAM6 antigen and decrease its invasiveness. Treatment of BxPC3 tumor cells with 2A3 or 2A3-Fc reduces cell proliferation, invasion, and MMP-9 activity. Such treatment also reduces the ability of the conditioned media of pancreatic tumor cells to promote HUVEC cell angiogenesis. An advantage of these antibodies over drugs used for chemotherapy is that they are more specific for tumors that over-express CEACAM6 antigen. Therefore, this might result in reduced general cell toxicity and cancer cell chemo-resistance. Additionally, single-domain antibodies such as 2A3 are known to possess stability; they show ease in antibody engineering; and have superior tissue penetration ability due to their small size. The Fc-fusion version (2A3-Fc) is also advantageous for its long half life in circulation, and its ability to induce antibody-dependent cellular cytotoxicity and complement-dependent cytotoxicity.

The present invention will be further illustrated in the following examples. However, it is to be understood that these examples are for illustrative purposes only and should not be used to limit the scope of the present invention in any manner.

Example 1

Cell Culture

Human small cell lung carcinoma cell A549, human colon cancer cell LS174T, and human pancreatic cancer cell BxPC3 were obtained from the American Type Culture Collection (ATCC), and murine breast cancer cells JM01 were obtained from Dr. M. O'Connor (National Research Council of Canada, Montreal, Canada); the cells were cultured in DMEM, EMM, RPMI, DMEM (Invitrogen, Carlsbad, Calif.) media, respectively, supplemented with 10% fetal bovine serum (FBS, Roche). Human head and neck squamous carcinoma cell line UM-SCC-22B was obtained from the University of Michigan and maintained in RPMI 1640 medium supplemented with 10% fetal bovine serum (FBS) and 1% glutamine. Human umbilical vein endothelial cells (HUVECs) were obtained from Invitrogen and were cultured in Medium 200 (Invitrogen) supplemented with 15% complement inactivated FBS and 2% low serum growth supplement (Invitrogen). All of the cell culture media contained 100 units/ml penicillin and 100 µg/ml streptomycin. Cells were grown at 37° C., 5% $CO_2$ in 6-well microtiter plates for 24 hours. For immunocytochemical staining (Example 8), the cells were cultured on sterile cover slips in 6-well microtiter plates until approximately 80% confluent.

Example 2

Isolation of sdAb

Single domain antibodies (sdAb) were generated by immunization of a llama and subsequently isolated.

Figure 1A:
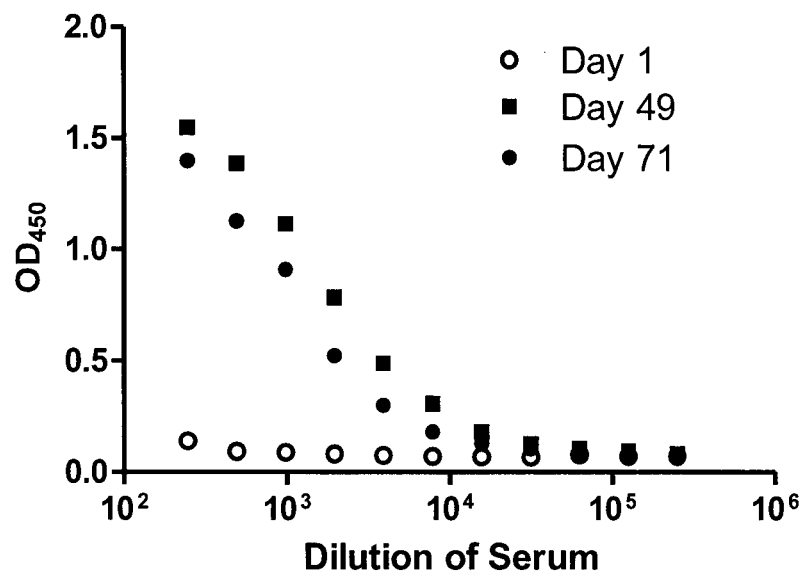
FIG. 1A shows the IgG immune response against recombinant CEACAM6 of a llama immunized with cells from 4 different tumor cell lines, as measured by ELISA. The day 1 (open circle), day 49 (filled circle) and day 71 (filled square) immune responses to coated CEACAM6 were detected with anti-llama antibody.

One llama (*Llama glama*) was immunized five times (days 1, 21, 35, 49, and 63) subcutaneously with $1 \times 10^7$ whole cells from each of the four cells lines of Example 1. Complete Freund's adjuvant, incomplete Freund's adjuvant and no adjuvant was applied to the first, the second to the forth, and the fifth immunization, respectively. On days 1, 22, 36, 49, 64 and 71, 50 ml blood was collected from which sera and peripheral blood lymphocytes were isolated. An antigen-specific immune response against CEACAM6 was observed at both day 49 and day 71 compared to pre-immune level (FIG. 1A), despite the fact that purified recombinant CEACAM6 was never used for immunization of the llama.

RNA was extracted from peripheral blood lymphocytes using QIAamp RNA Blood Mini Kit (Qiagen, Mississauga, ON). cDNA was synthesized using First-Strand cDNA Synthesis Kit (GE Healthcare, Baie d'Urfé, QC). Primers "MJ1.2.3 Back"

MJ1:
(SEQ ID NO: 9)
5'-GCCCAGCCGGCCATGGCCSMKGTGCAGCTGGTGGAKTCTGGGGGA-3'

MJ2:
(SEQ ID NO: 10)
5'-GCCCAGCCGGCCATGGCCCAGGTAAAGCTGGAGGAGTCTGGGGGA-3'

MJ3:
(SEQ ID NO: 11)
5'-GCCCAGCCGGCCATGGCCCAGGCTCAGGTACAGCTGGTGGAGTCT-3' and "$CH_2+CH_2b_3$" (described elsewhere (Doyle et al, 2008))

(SEQ ID NO: 12)
$CH_2$: 5'-CGCCATCAAGGTACCAGTTGA-3'

(SEQ ID NO: 13)
$CH_2b_3$: 5'-GGGGTACCTGTCATCCACGGACCAGCTGA-3' were used to amplify the variable domains of both $V_HH$ (600 bp) and $V_H$ (900 bp). These two fragments were separated in agarose gel and the $V_HH$ fragment was purified from the gel. A nested PCR, using primers MJ7 and MJ8 (Doyle et al, 2008)

MJ7:
(SEQ ID NO: 14)
5'-CATGTGTAGACTCGCGGCCCAGCCGGCCATGGCC-3'

MJ8:
(SEQ ID NO: 15)
5'-CATGTGTAGATTCCTGGCCGGCCTGGCCTGAGGAGACGGTGACCTGG-3' was performed to amplify all $V_HH$ genes. The final PCR fragments were ligated into the phagemid vector pMED1 (Arbabi-Ghahroudi et al, 2009) using the restriction sites SfiI. The ligated vector was used to transform electrocompetent E. coli cells (TG1).

The $V_HH$ repertoire was expressed on phage after being rescued with M13K07 helper phage. Specific $V_HH$s against CEACAM6 were enriched by two rounds of in vitro selection on microtiter plates coated with the antigen, the N-terminal domain of CEACAM6 (10 µg/ml). The binding of the specific $V_HH$ carrying phage particles were performed in the competition of 100 µg/ml ES1 (the pentabody of the anti-CEACAM6 sdAb, AFAI; Zhang et al, 2004a). 100 mM triethylamine (pH 11.0) was used to elute bound phage particles which were immediately neutralized with 1 M Tris-HCl (pH 7.4) and were used to infect exponentially growing TG1 cells. To assess the enrichment of phage particles carrying antigen-specific $V_HH$s, a serial dilution of the phages eluted from antigen coated versus non-coated wells was used to transfect the exponentially growing TG1 cells.

Individual colonies obtained after second round of panning were tested against CEACAM6 in a phage ELISA. Briefly, clones were grown in 2xYT medium+ampicillin (100 mg mL$^{-1}$)+0.1% glucose medium to OD$_{600}$=0.3-0.5, and infected with M13K07 helper phage (37° C. no shaking, 30 min) followed by addition of kanamycin (50 µg mL$^{-1}$) and amplification overnight (37° C. with shaking). Cultures were centrifuged (4000 rpm, 20 min, 4° C.) to pellet the cells. Subsequently 100 µL of supernatant containing recombinant phage particles were added to pre-coated microtiter plate wells. After 2 hr incubation at 37° C., microtiter plate wells were washed three times with PBST followed by addition of anti-M13 HRP conjugate (1:5000). $V_HH$-phages bound to CEACAM6 were detected by the addition of 100 µL of HRP substrate (KDL) for 15 minute incubation and the reaction was stopped using 1 M H$_3$PO$_4$ and absorption at 405 nm was measured.

The $V_HH$s cloned in the pMED1 phagemid vector and transformed into E. coli yielded a $V_HH$ library with 5×10$^8$ independent transformants and 85% insertion rates, giving it a functional library size of 4.3×10$^8$. This library was used to select CEACAM6-binding sdAb as described (Els Conrath et al, 2001) with the exception that only two rounds of panning, in the presence of 100 µg/ml ES1 (the pentabody of the anti-CEACAM6 sdAb, AFAI; Zhang et al, 2004a) were performed. Addition of ES1 was made to avoid isolation of the sdAb AFAI, and to also suppress the chance of low affinity antibodies being isolated.

Figure 1B:
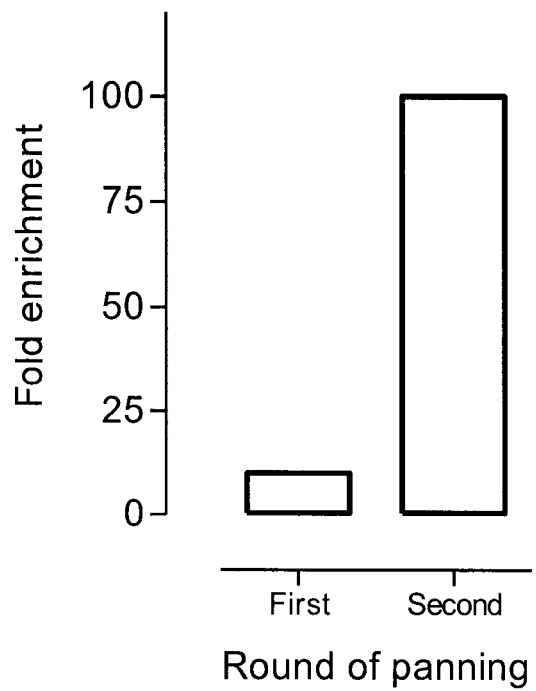
FIG. 1B is a graph showing the enrichment of CEACAM6 binding phagemids in different rounds of panning compared with non-specific binding.

Phage specifically binding to CEACAM6 was significantly enriched after the two rounds of panning, (FIG. 1B). Forty eight randomly picked clones were tested on phage ELISA to identify those displaying CEACAM6-specific sdAb, of which 18 scored positively. This may be due to the stringent washing conditions applied during panning. DNA sequencing revealed that the sdAb displayed in these clones were all the same, and was designated 2A3 (FIG. 1C). The 2A3 sdAb possesses the $V_HH$ hallmark amino acids substitutions in framework 2 (Val37Phe, Gly44Glu, Leu45Arg and Trp47Xaa, in Kabat numbering (Kabat et al, 1991a). The common camelid $V_HH$ Leu11Ser substitution is not seen in 2A3.

Example 3

Expression of sdAb

The sdAb 2A3 (Example 2) was subcloned into an expression vector for protein production and purification. The engineered 2A3 sdAb includes the ompA signal peptide as well as c-myc and His tags, and comprises the sequence:

(SEQ ID NO: 16)
MKKTAIAIAVALAGFATVAQAQPAMAQVKLEESGGGLVQAGGSLRLSCRT

SGRTNSVYTMGWFRQAPGKEREFVAQIMWGAGTNTHYADSVKGRFTISRD

SAESTVYLQMNSLKPEDTAVYYCAANRGIPIAGRQYDYWGQGTQVTVSSG

QAGQGSEQKLISEEDLNHHHHHH

The sdAb 2A3 was subcloned in the expression vector pMED2 (Arbabi-Ghahroudi et al, 2009) using the restriction enzyme SfiI. After sequence confirmation, recombinant sdAbs were expressed as 6xHis-tagged protein in the periplasm and purified by IMAC using a Ni-NTA column. Briefly, clones were inoculated in 25 mL LB with 100 µg/ml ampicillin and incubated at 37° C. with 200 rpm shaking overnight. 20 mL of the culture was transferred to 1 L of M9 medium (0.2% glucose, 0.6% Na$_2$HPO$_4$, 0.3% KH$_2$PO$_4$, 0.1% NH$_4$Cl, 0.05% NaCl, 1 mM MgCl$_2$, 0.1 mM CaCl$_2$) supplemented with 0.4% casamino acids, 5 µg/ml of vitamin B1 and 100 µg/ml ampicillin and incubated for 24 hr. 100 ml of 10×TB nutrients (12% Tryptone, 24% yeast extract and 4% glycerol), 2 ml of 100 µg/ml ampicillin and 1 ml of 1 M isopropyl-beta-D-Thiogalactopyranoside (IPTG) was added to the culture and incubation was continued for another 65-70 hr at 28° C. with a shaking speed of 200 rpm. Cells were then centrifuged and the pellets were lysed with lysozyme. Cell lysates were centrifuged and supernatants were loaded onto 5 ml HiTrap™ chelating HP affinity columns (GE Healthcare). After washing the columns with four column volume of wash solution (10 mM HEPES containing 500 mM NaCl, 20 mM immidazol, pH 7.5), His-tagged proteins were eluted with a linear gradient (2.5 to 500 mM) of immidazole and the eluted proteins were dialyzed in PBS buffer.

The one-step purification protocol described above resulted in protein with over 95% purity when assessed with SDS-PAGE (data not shown). The production yield was 25 mg purified protein per liter of bacterial culture. As most camelid sdAb, 2A3 exists as pure monomer seen as a single peak in a size exclusion chromatography using a Superdex75 column (FIG. 2).

Figure 1D:
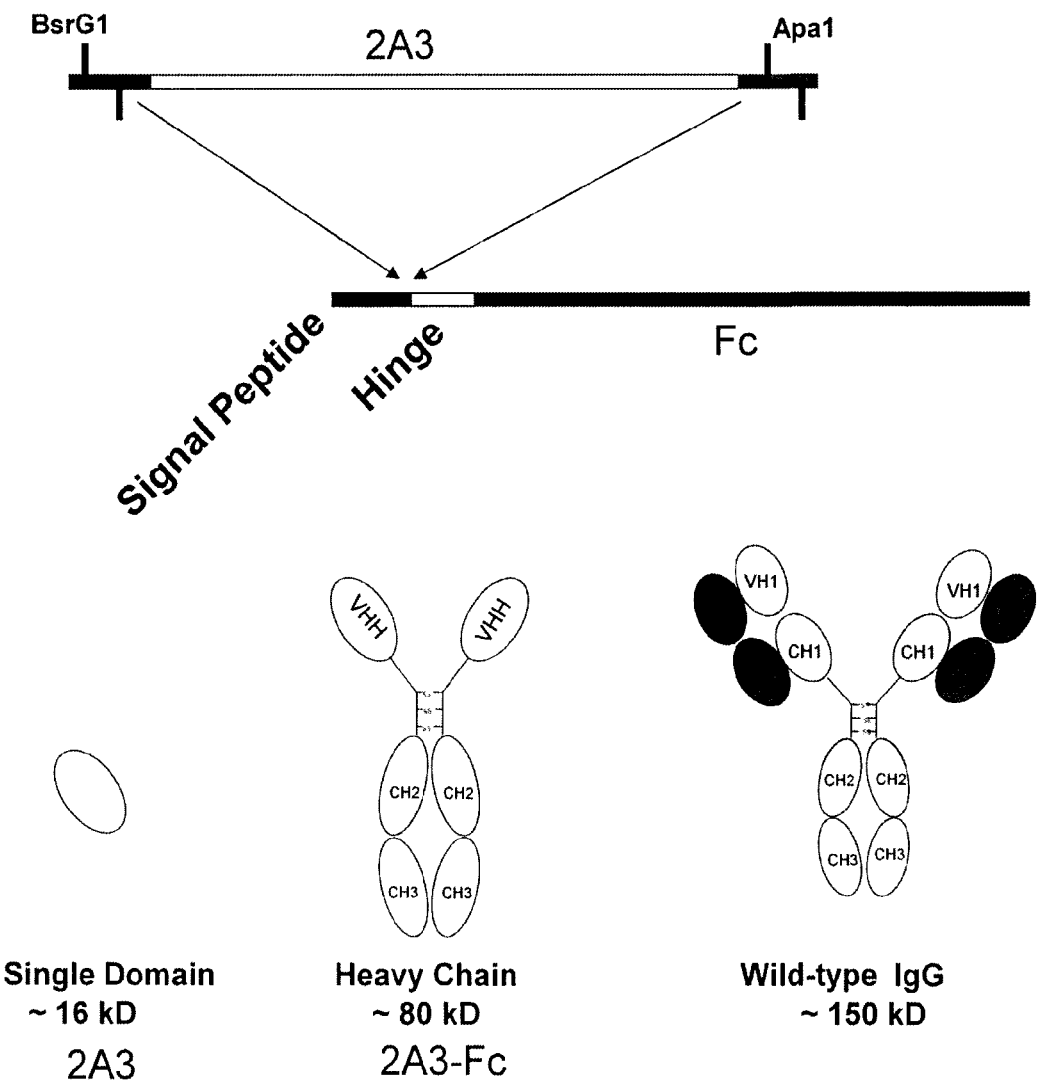
FIG. 1D shows the constructs (top) and schematic drawing (bottom, labelled Single Domain and Heavy Chain, respectively) of the 2A3 and 2A3-Fc antibodies. sdAbs are the variable regions of camelid heavy chain antibodies. They can be cloned and expressed either alone, or may be cloned and expressed in fusion with an Fc fragment of an antibody. In the present invention, the sdAb 2A3 was subcloned into a mammalian expression vector pTT5 with the mouse Fc2b fragment.

The 2A3 sdAb was cloned into mammalian expression vector pTT5 (Durocher & Perret, 2002) containing the mouse Fc2b fragment (FIG. 1D); the resulting 2A3-Fc protein was expressed and purified as described previously (Zhang et al, 2009a; 2009b). Briefly, 293-6E cells were grown in 293-SFM (Invitrogen, Burlington, ON) then transfected with the pTT5 constructs using PEI as a transfection agent. Transfected cells were allowed to grow for 5 days in F17 medium (Invitrogen, Carlsbad, Calif.). The cell culture medium was harvested by centrifugation, and then the medium was filtered using a 0.22 micron membrane to remove cell debris. 2A3-Fc was purified using a Protein G column (GE Healthcare, Piscataway, N.J.). More than 30 mg of >95% pure protein were obtained per liter of culture (FIG. 3).

Example 4

Biophysical Characterization of sdAb

The circular dichroism (CD) profile and the thermostability of sdAb 2A3 produced in Example 3 was determined.

Purity of proteins and their formation of aggregates or lack thereof were assessed by Superdex™ 75 10/300GL (GE Healthcare) size exclusion chromatography using an ÄKTA FPLC™ system (GE Healthcare). Proteins were separated with a Superdex™ 75 SEC in 10 mM phosphate buffer, pH 7.0. The 2A3 peak was collected, and the protein was used for CD analysis. CD spectra were collected from 250 to 200 nm at protein concentrations of 2.5 µM in a 10 mm quartz cuvette with a J-850 CD spectrometer (JASCO, Easton, Md.). Data were collected with a band width of 1.0 nm and a scanning speed of 50 nm/min with two accumulations of scans to determine the CD profile of the profile. Under the same conditions but with a single data accumulation, CD spectra were automatically measured at 2° C. intervals from 25 to 91° C. to determine thermal denaturation of the protein at a temperature shift speed of 1° C./min. Ellipicity at 217 nm were plotted against temperature and $T_m$s were calculated from Boltzmann Sigmoidal equation using GraphPadPrism software.

Figure 4A:
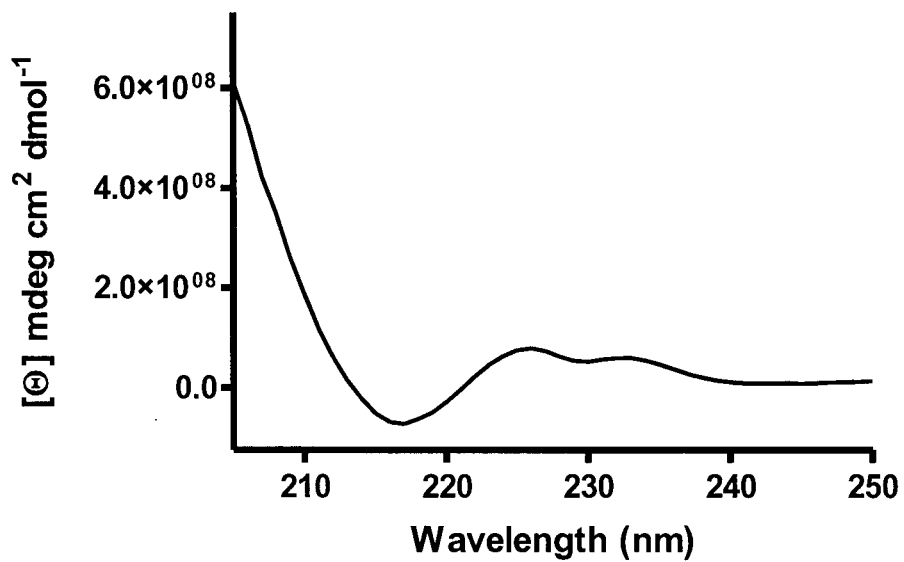
FIG. 4A shows the CD profile of 2A3 measured at room temperature.
Figure 4B:
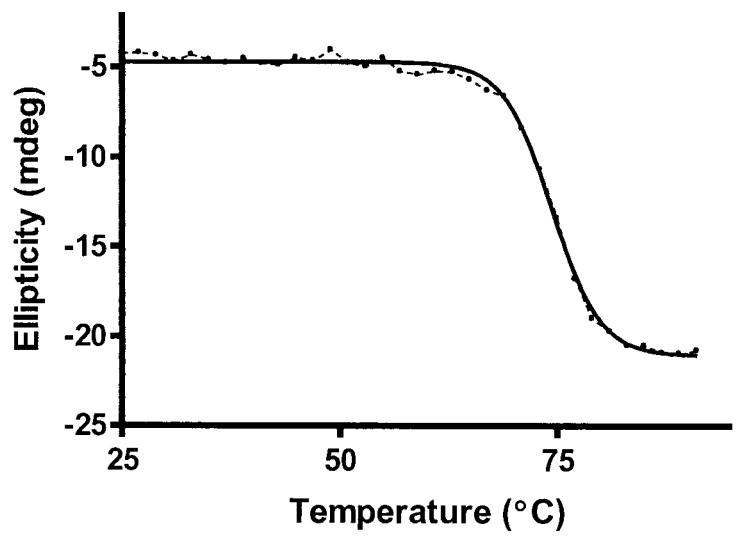
FIG. 4B shows the CD analysis of the melting temperature ($T_m$) measurement of 2A3. The CD values measured at 217 nm are plotted against temperature ranging from 25 to 91 (dotted line with the squares). The solid line shows the fitted values using GraphPad Prism program.

Circular dichroism (CD) profile of 2A3 was measured to estimate the secondary structure and thermostability of the sdAb. 2A3 had the typical CD profile for single domain antibodies (FIG. 4A). Thermo-induced denaturation of the protein was measured in the temperature range from 25 to 91° C. with 2° C. intervals. Plotting the CD value at 217 nm to temperature suggested a two phase denaturation (FIG. 4B) with a calculated melting temperature ($T_m$) of 74° C.

Example 5

Solid-Phase ELISA of sdAb

The sdAb 2A3 of Example 3 was further evaluated for its ability to retain its binding capacity in serum.

Maxisorb 96-well microtiter plates (Nunc) were coated with 2 µg/ml recombinant CEACAM6 protein (N-domain) overnight at 4° C. in phosphate-buffered saline (PBS). 2% fat-free dry milk solution in PBS was used for 2 h at room temperature to block the residual protein-binding sites in the wells. Serial diluted serum or soluble recombinant sdAbs were added to the wells, which were incubated at 37° C. for 24 hr. Detection of llama IgGs and sdAb was performed with goat anti-llama IgG (Bethyl Lab, Montgomery, Tex.), horseradish peroxidase anti-goat conjugate (Cedarlane, Burlington, ON) and the corresponding substrate KPL for peroxidase. The reaction was stopped by adding 1 M $H_3PO_4$ and the absorption at 405 nm was measured.

Figure 5A:
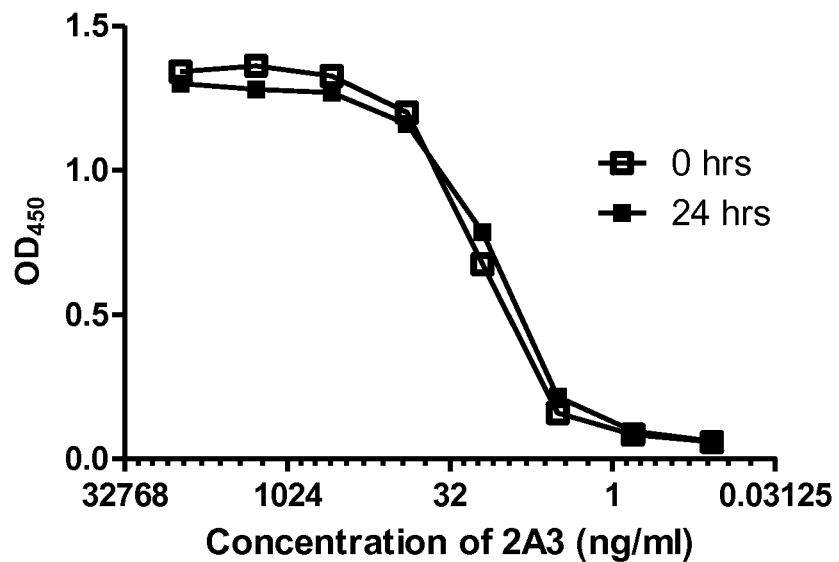
FIG. 5A is a graph showing the CEACAM6 binding capability of 2A3 after 24 hrs of incubation in mouse serum at 37° C. compared with its initial binding function (0 hr) as measured in ELISA. The 1/5 serial dilution was started at 10 µg/ml concentration.

The sdAb was incubated in mouse serum and the residual binding capacity was measured by ELISA then compared with the same antibody that was not incubated in serum. The result (FIG. 5A) showed that 2A3 retained its full binding capacity under this condition, suggesting that either the sdAb alone or antibodies built thereon should be resistant to proteolysis caused by serum proteases—a premise for their in vivo application.

Example 6

Affinity Measurement of sdAb

The affinities of the 2A3 sdAb and 2A3-Fc of Example 3 as well as antibody 9A6 (Santa Cruz Biotechnology; Santa Cruz, Calif.) to CEACAM6 N-domain were determined with surface plasmon resonance (SPR).

Binding of sdAb 2A3 to CEACAM6 was determined by SPR using a Biacore 3000 (GE Healthcare). 209 RUs of CEACAM6 and 1746 RUs of Ovalbumin (as reference protein) were immobilized on research grade sensor chip CM5 (GE HealthCare). Immobilizations were performed with an amine-coupling kit (GE Healthcare) and carried out at 50 µg/ml CEACAM6 in 10 mM Acetate, pH 4 (GE Healthcare) and 50 µg/ml of Ovalbumin in 10 mM Acetate, pH 4.5. 120 µL of the sdAb at concentration of 1 nM to 60 nM were injected over the surfaces at a flow rate of 40 µl/min. Analyses were carried out at room temperature in HBS-EP, 10 mM HEPES pH 7.4, 150 mM NaCl, 3 mM EDTA and 0.005% surfactant P20 (GE Healthcare). Regeneration was performed with running buffer (HBS-EP). Data were analyzed with BIAevaluation software 4.1.

Similarly, the binding affinities of 9A6 and 2A3-Fc antibodies were determined using a Biacore 3000 (GE Healthcare). A total of 2179 resonance units (RUs) of 2A3-Fc, 4438 RUs of 9A6, and 3745 RUs of Ovalbumin were immobilized on to a CM5 research grade sensor chip (GE HealthCare). One hundred twenty microliters of CEACAM6 recombinant protein at concentration of 0.1 nM to 200 nM was injected over the surfaces at a flow rate of 40 µl min-1. Analyses were carried out at room temperature in HBS-EP comprising 10 mM HEPES pH 7.4, 150 mM NaCl, 3 mM EDTA and 0.005% surfactant P20 (GE Healthcare). Regeneration was performed with HBS-EP used as running buffer. The data were analyzed by using BIAevaluation software 4.1.

Figure 5B:
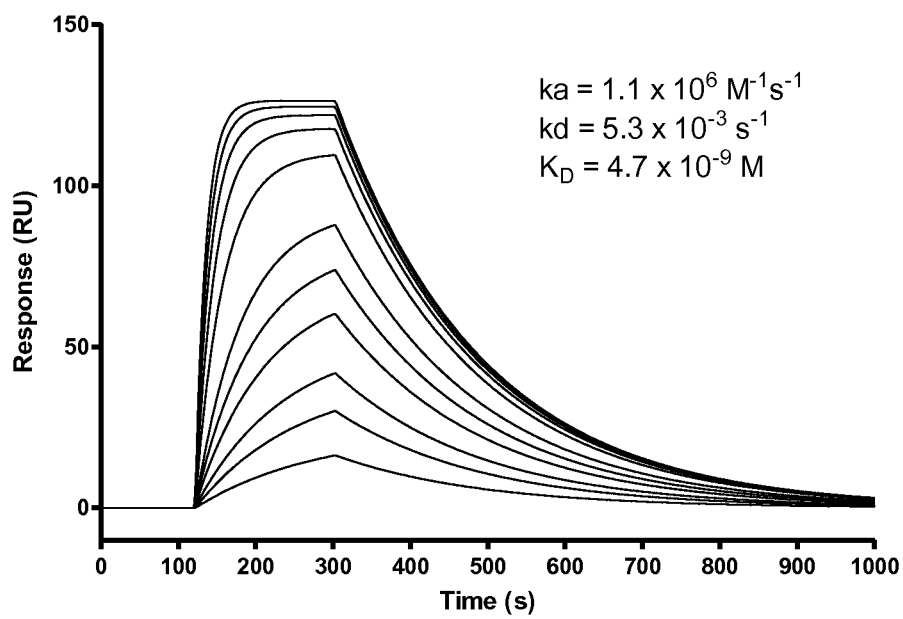
FIG. 5B shows Biacore profiles obtained in the calculation of 2A3 affinity to recombinant CEACAM6 by surface plasmon resonance (SPR); Biacore profiles of 2A3 at concentrations ranging from 1 to 60 nM were fit to a 1:1 Langmuir binding model using BIAevaluation 4.1.
Figure 5C:
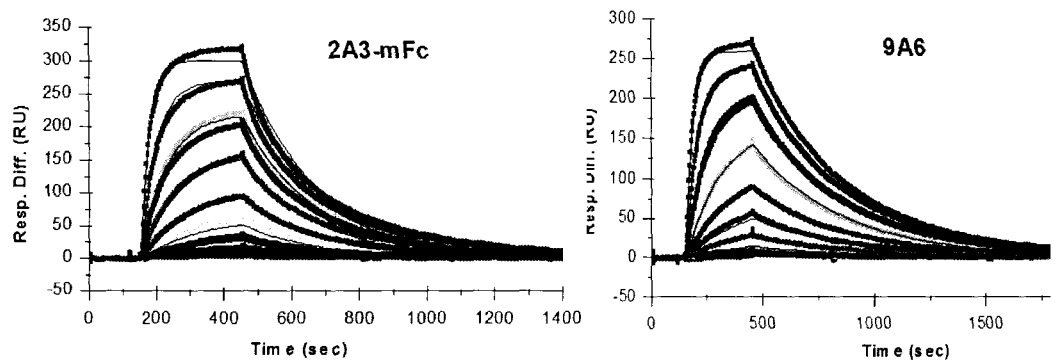
FIG. 5C shows Biacore profiles of 2A3-Fc (left) and 9A6 (right).

Injection of 2A3 onto CEACAM6-coupled surface revealed specific binding of the sdAb to the antigen. The actual association and dissociation curves fit well to the 1:1 Langmuir binding model, giving an association rate ($k_a$) of $1.1 \times 10^6 M^{-1} s^{-1}$, a dissociation rate ($k_d$) of $5.3 \times 10^{-3} s^{-1}$, and a dissociation constant ($K_D$) of $4.7 \times 10^{-9}$ M (FIG. 5B). Affinity constants ($K_D$s) for 9A6 and 2A3-mFc were 8 nM and 13 nM, respectively (FIG. 5C)

Example 7

Epitope Mapping

Epitope mapping was performed using CEACAM6 and the sdAb 2A3 produced in Example 3.

A peptide array for the N-terminal domain of CEACAM6 protein sequence was synthesized by JPT (Berlin, Germany). A total of 45 peptides with 15 amino acid length, and 10 amino acid overlapping were synthesized. The peptide array membrane was probed with the isolated sdAb 2A3, and then detected with anti-llama antibody according to manufacturer's recommendations.

Figure 5D:
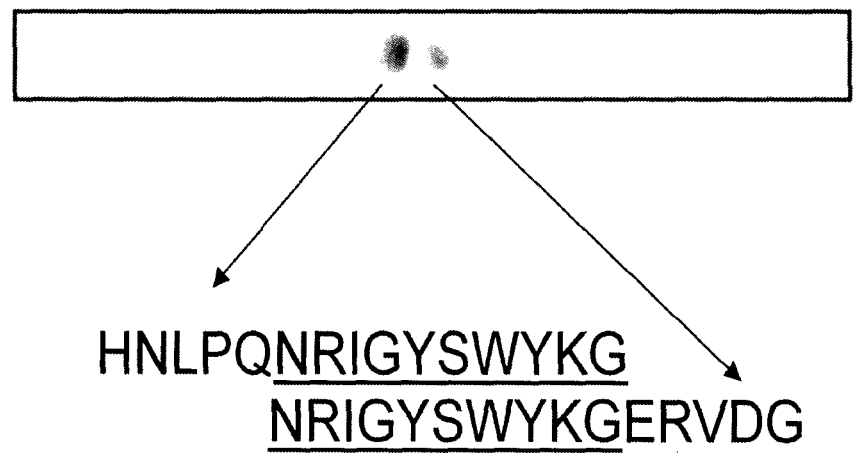
FIG. 5D shows results of epitope mapping of the sdAb 2A3. Two spots (top) corresponding to two CEACAM6 peptides (bottom; HNLPQNRIGYSWYKG, SEQ ID NO:5.

Probing the peptide array membrane with 2A3 antibody revealed 2 specific spots (peptides) that show binding of the antibody. The common (shared) sequence for these peptides is NRIGYSWYKG (SEQ ID NO:7; FIG. 5D) which would be part of the BC loop and part of the C strand based on the published structure of the hCEACAM1 N-domain (Fedarovich et al, 2006).

Example 8

Immunocytochemical Staining and Flow Cytometry with sdAb

The isolation of CEACAM6-specific sdAb 2A3 and its biochemical characterization was conducted using recombinant CEACAM6 expressed in *E. coli*. It was examined whether 2A3 and 2A3-Fc bind to mammalian-expressed CEACAM6.

For immunocytochemical staining, the cells of Example 1 grown on the cover slip were first fixed in 10% formaldehyde in PBS for 10 minutes. After washing the cells with PBS, 2% skimmed milk in PBS was added in the chambers and incubation was allowed for 2 hours to block unspecific bindings. After washing the blocking solution, cells were incubated with FITC-labeled sdAb. Counter staining was performed with DAPI (0.1 μg mL$^{-1}$, Invitrogen). Following immunostaining the cover slips were mounted using the Prolong Antifade Kit (Invitrogen) and observed under an Olympus BX51 fluorescent microscope.

For flow cytometry, purified sdAbs were labelled with FITC as instructed by the manufacturer (Invitrogen). Different cell lines were grown as a monolayer until they were approximately 80% confluent. After fixing by 10% formaldehyde in PBS for 10 minutes, cells were washed with PBS then incubated at room temperature with different FITC-labelled sdAbs. After one hour of incubation, cells were washed twice with PBS to remove unbound sdAbs and the cells were analyzed by flow cytometry using a FACS Canto flow cytometer (BD Bio-sciences).

Western blot analysis against mammalian-expressed recombinant CEACAM6 using 2A3 as the antibody (FIG. 6A) clearly shows that 2A3 recognized the protein; thus, mammalian-expressed CEACAM6 resembles native CEACAM6 more than that expressed by *E. coli*. Furthermore, in the same Western blot, 2A3 showed clear binding to the total lysate of the BxPC3 cells, confirming its binding to the native protein (FIG. 6A).

For immunocytochemical staining, FITC-labelled 2A3 was incubated with formaldehyde-fixed pancreatic tumor cells BxPC3. FITC-2A3 showed strong staining to practically each BxPC3 cell (FIG. 6B). 2A3 also binds to other tumor cell lines such as colorectal cancer cell line LS174T and non-small cell lung carcinoma cell line A549 both at a lower intensity and to fewer cells (data not shown). Similar results were obtained when flow cytometry was used to analyze the binding. Whereas approximately 90% of BxPC3 cells were stained positive with 2A3, only about 16% LS174 and 20% A549 cells were stained positive (FIG. 6C).

In summary, BxPC3 cells had high expression levels that were detected by Western blotting of cell lysates, FACS analysis, and immuno-histochemical staining (FIG. 7). However, no CEACAM6 expression was detected in HUVECs or in the culture media of either type cells (FIG. 7B).

Example 9

In Vitro MTT Assay with sdAb

As CEACAM6 is implicated in tumor progression and sdAb 2A3 is a high affinity binder to CEACAM6 expressed on cell surface, the effect of this sdAb and the 2A3-Fc construct on cell proliferation was evaluated in an in vitro MTT assay.

The effect of the 2A3 sdAb and 2A3-Fc on cell proliferation and viability was evaluated via a proliferation assay (Mosmann et al, 1983) using 3-(4,5-Dimethylthiazol-2-yl)-2,5-diphenyltetrazolium bromide (MTT reagent, Sigma Aldrich); in some experiments, VTI1-Fc was used as a negative control. BxPC3 A549 and LS174 cells were plated in 96-well microtiter plates (Nunc) at a density of 5,000 cells/well, and 125 μg/ml antibody (2A3 as the test sdAb, and BSA12 (Li et al, 2009) as an irrelevant control sdAb) was added to the cells 24 hours later. Cells were left to grow for 72 h in the presence of the sdAb, then assayed for viability. Briefly, 20 μl of MTT reagent (2 mg/ml in PBS) was added to each well. After four hours, the supernatant was removed, adherent cells were lysed, and the crystals were solubilized with 100 μl dimethyl sulfoxide (DMSO, Sigma) per well. The absorbance of the formazan product was measured with a plate reader at a wavelength of 570 nm. After subtracting background absorbance, results were expressed as absorbance.

The cell lines BxPC3, A549 and LS174 were chosen as cell models due to their different expression levels of CEACAM6. The proliferation of BxPC3 cells as measured by MTT shows a significant difference (p<0.0001) between cells treated with BSA12, an irrelevant sdAb (Li et al, 2009), and sdAb 2A3 (FIG. 8A), suggesting 2A3 inhibits BxPC3 proliferation in vitro. In contrast, addition of 2A3 in the culture of A549 and LS174 cells had little effect on their growth (FIG. 8B). Given that these two latter cell lines have lower expression levels of CEACAM6, the differential growth inhibition ability towards different cells may be dependent on antigen expression levels.

Inhibition of cell proliferation of BxPC3 by 2A3-Fc, along with 2A3, was also tested by MTT assay. The 2A3 antibody at 50 μg/ml inhibited approximately 27% of cell proliferation in contrast to starvation medium control (FIG. 9A). The inhibition effect of 2A3-Fc was also tested at a concentration of 360 μg/ml, which is the molar concentration equivalent to 50 μg/ml of 2A3. 2A3-Fc had better inhibition effect, inhibiting 55% of BxPC3 cell proliferation.

Example 10

In Vitro Gelatin Zymography, MMP-2 and MMP-9 Activity Assay

Gelatin zymography is used to detect the activity of gelatinases, namely, matrix metalloproteinases MMP-2 and MMP-9 (28). The 2A3 and 2A3-Fc antibodies of Example 3 were used to test their influence on MMP-2 and MMP-9 activity.

Briefly, conditioned media were obtained from BxPC3 cell cultures that had been treated with 2A3 or 2A3-Fc antibody, or gemcitabine. The medium aliquots were taken from BxPC3 cultures at the time the proliferation assays (Example 9) were performed. For evaluation of dose-dependence effect, antibodies and gemcitabine were used at concentrations of 0.4-25 μM and 0.4-50 nM, respectively. The media were applied to a 10% sodium dodecyl sulfate-polyacrylamide gel electrophoresis gel (SDS-PAGE) that was supplemented with 1.5 mg/ml gelatin. The gel was run at 150 V until the bromophenol blue dye reached the bottom of the gel. SDS was removed from the gel by washing the gel four times with 2.5% Triton X-100 for 30 min at room temperature with gentle shaking using an orbital shaker (28). The gel was then incubated overnight at 37° C. in development buffer comprising 50 mM Tris-HCl, 0.2 M NaCl, 5 mM CaCl$_2$, 5 mM ZnCl$_2$, 0.02% Brij-35, and 0.05% NaN$_3$ at pH 7.4. Gelatinase-digested gelatine-supplemented gels were stained with Coomassie blue. Clean bands produced by MMP-2 and MMP-9 activity were visible against the blue background after destaining. The relative activities of the gelatinases were determined by using a densitometer (AlphaView, Fluor Chem SP, Alpha Innotech Corporation, San Leandro, Calif., USA).

Results indicate that both 2A3 and 2A3-Fc were able to reduce the activity of MMP-9, but not MMP-2 activity (FIG. 9B). The dose-dependence of the inhibition of BxPC3 cell proliferation and MMP-2 or MMP-9 activity was then investigated; the effect of gemcitabine was also tested. The 2A3/

2A3-Fc antibodies and gemcitabine decreased BxPC3 cell proliferation to less than 10% at dosages of 25 µM and 50 nM, respectively. The IC50s for 2A3, 2A3-Fc, and gemcitabine were determined as 6.5 µM, 8 µM, and 12 nM, respectively (FIG. 10A).

Anti-CEACAM6 antibodies down-regulated MMP-9 activity, but not MMP-2 activity in the BxPC3 cells (FIG. 10B). The culture medium MMP-9 activity of 2A3-treated BxPC3 was down-regulated by 33% compared to non-treated cells (FIG. 10B). Gemcitabine decreased BxPC3 cell proliferation more effectively than did the sdAb. However, this effect was due to cell toxicity—it did not lower the level of MMP9. Instead, a slightly increased MMP-9 activity was detected for the BxPC3 cells that were treated with gemcitabine.

Although gemcitabine profoundly affects cell survival, it does not affect MMP-2 and MMP-9 activity in BxPC3 cells. The effect of gemcitabine on MMP-2 and MMP-9 was similar to that which was noted in previous reports (Haq et al, 2000; Kunnumakkara et al, 2010). Here, in addition to inhibiting cell proliferation, MMP-9 activity in the culture medium was down-regulated by blocking CEACAM6 on the BxPC3 surface using 2A3 and 2A3-Fc anti-CEACAM6. A 5 µM dosage of sdAb 2A3 reduced MMP-9 activity to 25%, but did not influence MMP-2 activity significantly. On the other hand, sdAb 2A3 reduced BxPC3 invasiveness by ~73%. Except for its cell toxicity effect, gemcitabine did not affect angiogenesis or invasion; it even increased MMP-2/MMP-9 activity slightly (~10%) at high dosages.

Example 11

Matrigel Invasion Assay

Matrigel invasion assay is designed to evaluate the capability of cells to invade into matrigel, an indication of the capacity to metastasize.

The assay was carried out by using bio-coated Matrigel invasion chambers (BD Biosciences, Bedford, Mass.). Each chamber comprised an 8 µm pore size PET membrane, which had a thin layer of Matrigel basement. Only cells that could digest the matrix could migrate through the pores. BxPC3 cells cultured in starvation medium (RPMI 1640 with 0.1% FBS) in the presence (treated) or absence (non-treated) of 40 µM of 2A3 or 2A3-Fc were detached with cell dissociation buffer (Invitrogen) then were centrifuged at 300 g for 5 min. The cells were re-suspended in RPMI medium and seeded on the tops of insert wells at $1\times10^5$ cells/well density and cultured at 37° C. in a humidified $CO_2$ chamber. After 20 hrs, the non-invasive cells were scrubbed from the top of the insert well using a cotton-swab. The invasive cells on the bottom surface were stained with Calcein AM (Invitrogen) and were photographed with an Olympus BX51 microscope. All experiments were performed in triplicate.

BxPC3 cells were able to degrade the matrigel and migrate through the basement membrane. The invasiveness was reduced for BxPC3 cells that were treated with anti-CEACAM6 antibody 2A3 or 2A3-Fc, compared to the control (non-treated) cells (FIG. 11A). The invasiveness of the cells that were treated with 2A3 or 2A3-Fc decreased to 27.4% (27.4±8.4% and 27.4±4.8%, respectively) (FIG. 11B). Thus, BxPC3 cancer cell invasiveness can be modulated by targeting CEACAM6 using 2A3 or 2A3-Fc antibody.

Example 12

In Vitro Capillary Formation Assay

Angiogenesis is another critical step in the progression of pancreatic cancer. Relatively complex and dense micro-vessels are localized in pancreatic cancer tissue. Highly vascular tumors are associated with an increased risk of hepatic metastasis and a poor survival rate (Semenza, 2003). Anti-angiogenesis is a valid strategy when employing pancreatic cancer target therapy. Thus, the in vitro capillary formation assay was used to test the ability of conditioned media of sdAb-treated BxPC3 cells to inhibit HUVECs angiogenesis.

Approximately 200 µl of Geltrex reduced growth factor basement membrane matrix (Invitrogen) was plated on to a 9 mm diameter cell culture insert well which had a 0.45 µl pore size (Millipore, Billerica, Mass.). The matrix was then polymerized at 37° C. for 30 min. Conditioned media obtained from BxPC3 cells treated with 2A3 or 2A3-Fc antibody for 24 hrs was collected and used to re-suspend HUVECs at $1\times10^5$ cells/ml. HUVEC cells were then seeded onto the polymerized matrix at $5\times10^4$ cells per well. The cells were cultured at 37° C. for 16 h then stained with Calcein AM (Invitrogen) for 30 min. Photographs were taken at 100× magnification employing fluorescence microscopy (Olympus BX51). Three fields that were randomly chosen were captured and the lengths of the capillaries in each field were measured.

Figure 12:
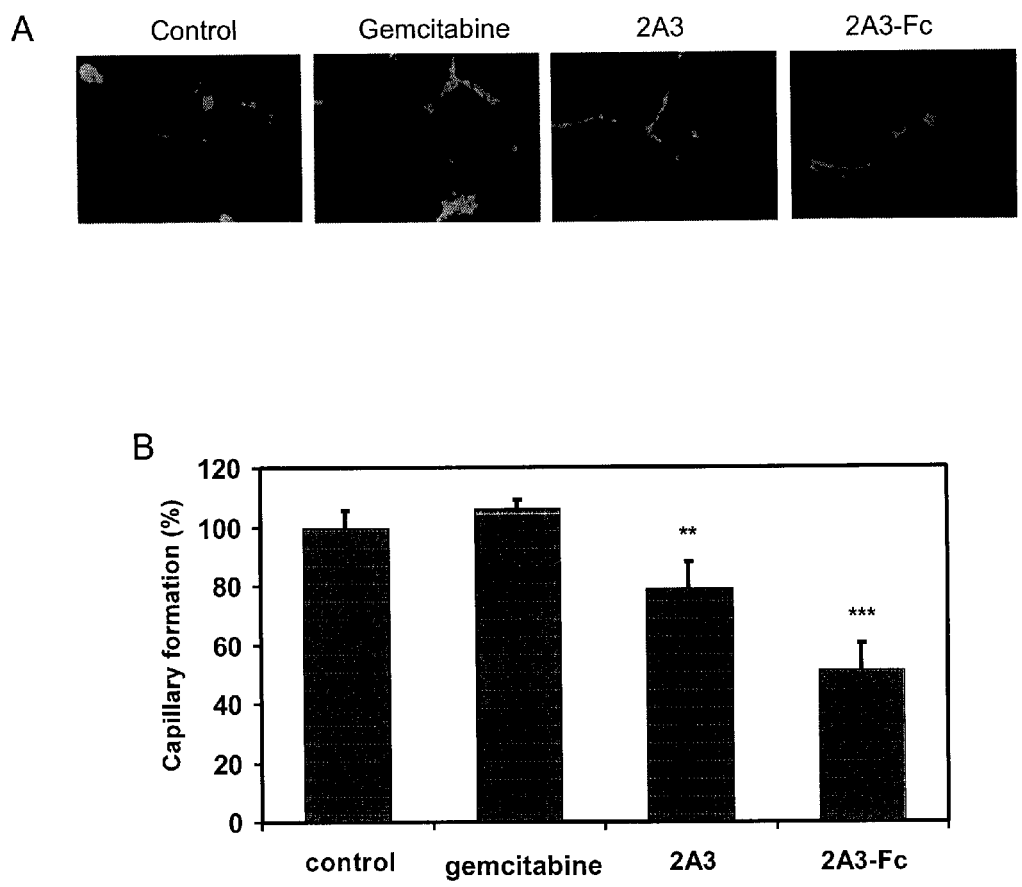

Results showed that tumor-induced angiogenesis was suppressed significantly when 2A3- and 2A3-Fc-treated BxPC3 culture medium was administered (FIG. 12). In this tubule formation assay, media from BxPC3 cells treated with 2A3 or 2A3-Fc decreased the total tube length significantly (the tubing formation activity was reduced by ~21%; FIG. 12A). The sdAb 2A3 inhibited 21% of endothelial cell angiogenesis; 49% of angiogenesis was inhibited by 2A3-Fc. In contrast, the inhibitory effects on angiogenesis were not seen when culture medium from gemcitabine-treated BxPC3 cells was used (FIG. 12B). Based on report that CEACAM6 plays a role in invasion and angiogenesis in pancreatic cancer, our results suggest that the role of CEACAM6 in invasion and angiogenesis in pancreatic cancer can be blocked by 2A3 or 2A3-Fc antibodies. Furthermore, as anti-angiogenic agents permit better delivery of gemcitabine into tumor vascular and interstitial spaces (Schwarz et al, 2009), 2A3 and 2A3-Fc sdAbs may also have such functions.

Example 13

Immunofluorescence Staining

2A3, 2A3Fc and 9A6 antibodies were labelled with Fluorescein 5(6)-isothiocyanate (FITC; Sigma-Aldrich). FITC was dissolved in anhydrous dimethyl sulfoxide immediately before use then added to antibodies with a ratio of 50 µg per mg of antibody. The mixture was incubated and rotated at room temperature for 60 min for covalent conjugation. The unreacted FITC was removed by PD-10 column.

Immunostaining of both CEACMA6-negative UM-SCC-22B cells (negative control) and CEACAM6-positive BxPC3 cells grown in vitro, using FITC-conjugated antibodies showed strong fluorescence signal in BxPC3 cells with all three antibodies (2A3, 2A3Fc and 9A6). Also, most of the fluorescent signal localized on the cell membrane, due to the membrane distribution of CEACAM6 antigen (FIG. 13A).

In vitro immunofluorescence staining of tumors obtained from mice established as a human pancreatic cancer BxPC3 model (see Example 14) was performed. This was done to show that BxPC3 cells, grown as a tumor in mice, retained CEACAM6 expression after being grown in mice. Briefly, tumor samples were collected from tumor bearing mice after the tumor reached the size of 100 $mm^3$. Frozen tumor slices (5-µm thickness) were fixed with cold acetone for 10 min and dried in air for 30 min. The slices were rinsed with PBS for 2 min and blocked with 10% donkey serum for 30 min at room temperature. The tumor sections were stained with FITC-labelled antibodies 9A6, 2A3, and 2A3Fc. The fixed tumor sections were then incubated with the FITC-conjugated antibodies. The sections showed strong staining with anti-CEACAM6 antibodies (FIG. 13D; data not shown for 2A3), showing that these tumors retained CEACAM6 expression after growing in mice.

Example 14

PET Imaging

In a human pancreatic cancer BxPC3 model, which is known to highly express CEACAM6, the pharmacokinetics and tumor delivery of three antibodies with different sizes were evaluated and compared with by quantitative PET imaging.

Antibody Labelling:

Monoclonal antibody 9A6 was purchased from Santa Cruz Biotechnology (Santa Cruz, Calif.). The 2A3 sdAb and 2A3-Fc were produced as described in Example 3. Antibodies were then labelled with FITC (Sigma-Aldrich; St. Louis, Mo.) or DOTA (Macrocyclics; Dallas, Tex.) according to previously reported methods, with minor modification (21-22). The reaction ratio of DOTA to 9A6, 2A3-Fc and 2A3 were 20:1, 10:1 and 2:1 respectively. $^{64}CuCl_2$ (74 MBq; National Institutes of Health) was diluted in 300 µl of 0.1 M sodium acetate buffer (pH 6.5) and added to 50 µg of DOTA-conjugated antibodies. The reaction mixture was incubated for 1 h at 40° C. with constant shaking. $^{64}$Cu-DOTA-Abs were then purified by PD-10 column (GE HealthCare; Piscataway, N.J.) using PBS as the mobile phase. Complexation of $^{64}$Cu and the conjugated antibodies was monitored by radio-TLC ($R_f^{64}$Cu-DOTA-9A6=0.032, $R_f^{64}$Cu-DOTA-2A3-Fc=0.076, $R_f^{64}$Cu-DOTA-2A3=0.090, $R_f^{64}$Cu=0.779). Radio-TLC was performed on an AR-2000 Bioscan scanner (Washington D.C.), using silica gel plates (LK6DF, 60 Å, 200 mm, Whatman) and 1% ethylenediaminetetraacetic acid (EDTA), 5% NH4OAc in water:methanol (1:1) as a developing solvent. Radio-TLC showed incorporation of greater than 95% for 9A6 and 2A3-Fc and 50% for 2A3.

Cell Uptake and Efflux Studies:

Cell uptake, internalization, and efflux of $^{64}$Cu-DOTA-2A3-Fc were performed with BxPC3 and UM-SCC-22B tumor cells (negative control). For cell uptake, the cells were seeded into 24-well plates at a density of $1\times10^5$ cells per well and incubated with 18.5 kBq (0.5 µCi/5 ng)/well of $^{64}$Cu-labelled tracer at 37° C. for 15, 30, 60, and 120 min. The cells were then washed three times with chilled PBS and lysed with 500 µL 0.1 M NaOH. For efflux studies, about 18.5 kBq (0.5 µCi)/well of $^{64}$Cu-DOTA-2A3-mFc were first incubated with BxPC3 cells in 24-well plates for 2 h at 37° C. The cells were washed three times with chilled PBS and allowed to stand with fresh buffer. At various time points, the medium was removed and the cells washed three times with chilled PBS. The cells were then lysed with 500 µL 0.1 M NaOH. The cell lysate was collected and the remaining radioactivity was measured in a γ counter (Packard, Meriden, Conn.). The cell uptake, and efflux were expressed as the percentage of the added dose (% AD) after decay correction. All experiments were performed with triplicate wells.

Along with time, the BxPC3 cells showed increased accumulation of radioactivity. After 2 hr incubation, the total uptake was 10.13±0.05% of total added dose. At the same time, the cells almost showed no uptake of $^{64}$Cu-DOTA-IgG. 22B cells showed much lower uptake of $^{64}$Cu-DOTA-2A3-Fc compared with BxPC3 cells (FIGS. 13B and C). These results confirmed the specific binding of $^{64}$Cu-DOTA-2A3-Fc to BxPC3 cells via CEACAM6 reorganization. When the labelled cells were incubated in serum-free medium devoid of radioactivity, $^{64}$Cu-DOTA-2A3-Fc showed slow dissociation and efflux from the cells with time slowly (FIG. 13B). After 2 h incubation, more than 65% of the radioactivity was still retained on the cells.

Small Animal PET and Image Analysis:

Subcutaneous BxPC3 tumor model was established in 5 to 6-week-old female athymic nude mice obtained from Harlan (Indianapolis, Ind.); $5\times10^6$ cells suspended in 50 µl of phosphate buffered saline (PBS) were injected and the mice underwent small animal PET studies when the tumor volume reached 100-200 mm³ (3-4 weeks after inoculation). PET scans and image analysis were performed using an Inveon microPET scanner (Siemens Medical Solutions). About 3.7 MBq (100 µCi/5 µg) of $^{64}$Cu-DOTA-Abs were administered via tail vein injection under isoflurane anesthesia. Five-minute static PET images were acquired at different time points post-injection (p.i.; n=4/group). The images were reconstructed using a two-dimensional ordered-subset expectation maximization (2D OSEM) algorithm, and no correction was applied for attenuation or scattering. For each scan, regions of interest (ROIs) were drawn over the tumor and major organs using vendor software (ASI Pro 5.2.4.0) on decay-corrected whole-body coronal images. The radioactivity concentrations (accumulation) within the tumors, muscle, liver, and kidneys were obtained from mean pixel values within the multiple ROI volume and then converted to MBq per milliliter per minute using the calibration factor determined for the Inveon PET system. These values were then divided by the administered activity to obtain (assuming a tissue density of 1 g/ml) an image-ROI-derived percent injected dose per gram (% ID/g). Results are shown in FIG. 14.

Due to its smaller size, $^{64}$Cu-DOTA-2A3 showed tumor accumulation as early as 30 min p.i. Both liver and kidneys showed very high radioactivity, indicating both hepatobiliary and renal-urinary clearance of this sdAb. In contrast, $^{64}$Cu-DOTA-2A3-Fc showed much slower tumor accumulation. At 4 hr p.i., the tumors were visualized clearly and the accumulation kept increasing with time. As for the full length antibody 9A6, the tumor uptake was much more delayed than 2A3-mFc. Liver and heart also showed high radioactivity with either 9A6 or 2A3-Fc as imaging probe. The kidneys were not visible with these two Abs (FIG. 15). Labelled murine IgG was used as control antibody, with the BxPC3 showing much lower uptake, representing non-specific perfusion of the IgG to tumor region.

The accumulation of $^{64}$Cu-DOTA-Abs on the tumor and major organs was quantified based on PET images and shown in FIG. 16. For 2A3, the tumor showed highest uptake at 30 min p.i. with a % ID/g of (4.22±1.13% ID/g), which decreased gradually to 3.85±0.37% ID/g at 2 hr p.i. The kidneys showed extremely high accumulation, reaching 102.7±3.15% ID/g at 60 min. Liver showed similar level of radioactivity as tumors. The tumor uptake of $^{64}$Cu-DOTA-2A3-Fc kept increasing time, specifically 11.8±2.66, 22.7±5.90, 43.1±6.78 and 98.2±6.12% ID/g at 2, 4, 8 and 24 hr p.i., respectively. The liver uptake dropped from 23.4±2.68% ID/g at 30 min to 10.6±1.14% ID/g at 24 hr. The $^{64}$Cu-DOTA-9A6 showed similar pattern as 2A3-Fc, with lower tumor uptake. At 24 hr, the tumor uptake was 57.8±3.73 and liver uptake was 11.6±1.53. The tumor uptake of 64Cu- DOTA-IgG was 8.33±1.66% ID/g at 24 hr, which was significant lower than that of both $^{64}$Cu-DOTA-9A6 and $^{64}$Cu-DOTA-2A3-Fc.

Tumor/non-tumor ratios of the three tracers are listed in Table 1. 2A3 showed decent tumor/blood ratio at very early time point and kept increasing with the time, from 3.90±1.47 at 30 min to 8.51±1.12 at 2 hr p.i. The tumor/muscle ratio was even higher. However, the tumors had almost no contrast to the liver. As for 2A3-Fc, the tumor/blood ratio was very poor at the early time points until 8 hr after tracer injection. At 24 hr after injection, the tumors showed excellent contrast to background with tumor/blood ratio of 9.25±1.64, tumor/liver ratio of 9.29±0.43 and tumor/muscle ratio of 36.1±13.9. The clearance of 9A6 was slower than that of 2A3-mFc, with a tumor/blood ratio of 3.61±0.28, tumor/liver ratio of 5.06±1.04 and tumor/muscle ratio of 29.9±2.26 at 24 hr p.i.

within the tumor. DAPI staining was used to show cells nuclei. The slides were observed with an epifluorescence microscope (Olympus, X81) (FIG. 17).

As shown in FIG. 17, for 9A6, the fluorescent signal was primarily detected within several cell diameters of the blood vessels. The 2A3-Fc fluorescent signal was limited to peri-vascular region with longer diffusive distance. Co-staining with CD31 further demonstrated limited peri-vascular localization of both 9A6 and 2A3-Fc in BxPC3 tumors. These results indicate that 2A3-Fc has a better penetration through perivascular tissues than the full length antibody 9A6. In addition, it also demonstrated that both 9A6 and 2A3-Fc retain their immunoreactivity after DOTA conjugation.

The embodiments and examples described herein are illustrative and are not meant to limit the scope of the invention as claimed. Variations of the foregoing embodiments, including

TABLE 1

Tumor/non-tumor ratios of $^{64}$Cu-DOTA-Abs in BxPC3 tumor bearing mice (n = 4/group)

|  |  | 30 min | 1 hr | 2 hr | 4 hr | 8 hr | 24 hr |
|---|---|---|---|---|---|---|---|
| 2A3 | T/B | 3.90 ± 1.47 | 6.94 ± 2.01 | 8.51 ± 1.12 |  |  |  |
|  | T/L | 1.07 ± 0.20 | 1.25 ± 0.25 | 1.15 ± 0.16 |  |  |  |
|  | T/K | 0.05 ± 0.02 | 0.04 ± 0.00 | 0.04 ± 0.01 |  |  |  |
|  | T/M | 5.41 ± 1.15 | 9.13 ± 2.21 | 14.8 ± 6.46 |  |  |  |
| 2A3-mFc | T/B | 0.12 ± 0.04 | 0.23 ± 0.05 | 0.49 ± 0.07 | 1.07 ± 0.20 | 2.48 ± 0.15 | 9.25 ± 1.64 |
|  | T/L | 0.15 ± 0.03 | 0.24 ± 0.03 | 0.57 ± 0.10 | 1.20 ± 0.22 | 2.53 ± 0.22 | 9.29 ± 0.43 |
|  | T/M | 1.90 ± 0.51 | 2.65 ± 0.20 | 4.88 ± 0.86 | 13.9 ± 0.62 | 13.7 ± 3.69 | 36.1 ± 13.9 |
| 9A6 | T/B | 0.08 ± 0.02 | 0.09 ± 0.01 | 0.16 ± 0.04 | 0.39 ± 0.04 | 0.79 ± 0.08 | 3.61 ± 0.28 |
|  | T/L | 0.20 ± 0.08 | 0.19 ± 0.01 | 0.32 ± 0.07 | 0.73 ± 0.05 | 1.33 ± 0.05 | 5.06 ± 1.04 |
|  | T/M | 1.54 ± 0.63 | 1.28 ± 0.04 | 1.94 ± 0.56 | 5.03 ± 0.84 | 10.9 ± 3.10 | 29.9 ± 2.26 |

The results were presented as mean ± SD (n = 4). T, tumor; L, liver; K, kidneys; M, muscle.

Example 15

Ex Vivo Biodistribution

Immediately after PET imaging (Example 14), the tumor-bearing mice were sacrificed and dissected. Blood, tumor, major organs, and tissues were collected and wet-weighed. The radioactivity in the wet whole tissue was measured with a γ-counter (Packard). The results were expressed as percentage of injected dose per gram of tissue (% ID/g) for a group of 4 animals. For each mouse, the radioactivity of the tissue samples was calibrated against a known aliquot of the injected radiotracer and normalized to a body mass of 20 g. Values were expressed as mean±SD (n=4/group).

As shown in FIG. 16, the BxPC3 tumor uptake of 2A3 was 5.65±0.58% ID/g at 2 hr p.i. Consistent with PET imaging, 2A3-Fc showed highest tumor uptake at 24 hr p.i., which was 95.4±29.3% ID/g. The tumor uptake of 9A6 and IgG was 66.8±13.7 and 11.2±0.39% ID/g respectively.

Moreover, and to show the extent of penetration of the antibodies into the tumor tissue after injection of the different antibodies, frozen tumor slices (5-μm thickness), prepared from tumors mentioned above, were fixed with cold acetone for 10 min and dried in air for 30 min. The slices were rinsed with PBS for 2 min and blocked with 10% donkey serum for 30 min at room temperature. The tumor sections were stained with Cy3-conjugated donkey anti-mouse IgG (1:200), to illustrate the anti-CEACAM6 antibody that was bound to the tumor cells in vivo. The sections were also co-stained with rat anti-mouse CD31 antibodies for 1 hr at room temperature and visualized using Dylight 488-conjugated donkey anti-rat secondary antibody (1:200; Jackson ImmunoResearch Laboratories, Inc.) to illustrate the boundaries of the blood vessels alternatives, modifications and equivalents, are intended by the inventors to be encompassed by the claims. Furthermore, the discussed combination of features might not be necessary for the inventive solution.

REFERENCES

All patents, patent applications and publications referred to herein and throughout the application are hereby incorporated by reference.

Arbabi-Ghahroudi M., A. Desmyter, L. Wyns, R. Hamers, and S. Muyldermans, Selection and identification of single domain antibody fragments from camel heavy-chain antibodies. FEBS Lett 414 (1997) 521-526.

Arbabi-Ghahroudi M, To R, Gaudette N, Hirama T, Ding W, MacKenzie R, Tanha J. Aggregation-resistant VHs selected by in vitro evolution tend to have disulfide-bonded loops and acidic isoelectric points. Protein Eng Des Sel 2009; 22:59-66.

Armstrong T, Packham G, Murphy L B, et al. Type I Collagen Promotes the Malignant Phenotype of Pancreatic Ductal Adenocarcinoma. Clinical Cancer Research 2004; 10:7427-37.

Baselga J, Tripathy D, Mendelsohn J, Baughman S, Benz C C, Dantis L, Sklarin N T, Seidman A D, Hudis C A, Moore J, Rosen P P, Twaddell T, et al. Phase II study of weekly intravenous trastuzumab (Herceptin) in patients with HER2/neu-overexpressing metastatic breast cancer. Semin Oncol 1999; 26:78-83.

Bell, A., Wang, Z. J., Arbabi-Ghahroudi, M., Chang, T. A., Durocher, Y., Trojahn, U., Baardsnes, J., Jaramillo, M. L., Li, S., Baral, T. N., O'Connor-McCourt, M., Mackenzie, R. and Zhang, J. Differential tumor-targeting abilities of three single-domain antibody formats. Cancer Lett. 289, 81-90 (2010).

Birkedal-Hansen H, Yamada S, Windsor J, et al. Matrix metalloproteinases. Curr Protoc Cell Biol 2008; Chapter 10:Unit 10 8.

Blumenthal R D, Hansen H J, Goldenberg D M. Inhibition of adhesion, invasion, and metastasis by antibodies targeting CEACAM6 (NCA-90) and CEACAM5 (Carcinoembryonic Antigen). Cancer Res 2005; 65:8809-17.

Blumenthal R D, Leon E, Hansen H J, Goldenberg D M. Expression patterns of CEACAM5 and CEACAM6 in primary and metastatic cancers. BMC Cancer 2007; 7:2.7.

Buchegger F, Schreyer M, Carrel S, Mach J P. Monoclonal antibodies identify a CEA crossreacting antigen of 95 kD (NCA-95) distinct in antigenicity and tissue distribution from the previously described NCA of 55 kD. Int J Cancer 1984; 33:643-9.

Chothia C, Lesk A M. Canonical structures for the hypervariable regions of immunoglobulins. J Mol Biol. 1987; 196 (4):901-17.

Davies J., and L. Riechmann, Affinity improvement of single antibody VH domains: residues in all three hypervariable regions affect antigen binding. Immunotechnology 2 (1996) 169-179.

De Kruif, J. and Logtenberg, T. Leucine zipper dimerized bivalent and bispecific scFv antibodies from a semi-synthetic antibody phage display library. J. Biol. Chem. 271, 7630-7634 (1996).

Doyle P J, Arbabi-Ghahroudi M, Gaudette N, Furzer G, Savard M E, Gleddie S, McLean M D, Mackenzie C R, Hall J C. Cloning, expression, and characterization of a single-domain antibody fragment with affinity for 15-acetyl-deoxynivalenol. Mol Immunol 2008; 45:3703-13.

Dumoulin m., K. Conrath, A. Van Meirhaeghe, F. Meersman, K. Heremans, L. G. Frenken, et al., Single-domain antibody fragments with high conformational stability. Protein Sci 11 (2002) 500-515.

Durocher, Y., S. Perret, et al. (2002). "High-level and high-throughput recombinant protein production by transient transfection of suspension-growing human 293-EBNA1 cells." Nucleic Acids Res 30(2): E9.

Duxbury M S, Ito H, Benoit E, Ashley S W, Whang E E. CEACAM6 is a determinant of pancreatic adenocarcinoma cellular invasiveness. Br J Cancer 2004a; 91:1384-90.

Duxbury M S, Ito H, Benoit E, Waseem T, Ashley S W, Whang E E. A novel role for carcinoembryonic antigen-related cell adhesion molecule 6 as a determinant of gemcitabine chemoresistance in pancreatic adenocarcinoma cells. Cancer Res 2004b; 64:3987-93.

Duxbury M S, Ito H, Ashley S W, Whang E E. CEACAM6 cross-linking induces caveolin-1-dependent, Src-mediated focal adhesion kinase phosphorylation in BxPC3 pancreatic adenocarcinoma cells. J Biol Chem 2004c; 279:23176-82.

Duxbury M S, Ito H, Ashley S W, Whang E E. c-Src-dependent cross-talk between CEACAM6 and alphavbeta3 integrin enhances pancreatic adenocarcinoma cell adhesion to extracellular matrix components. Biochem Biophys Res Commun 2004d; 317:133-41.

Duxbury M S, Matros E, Ito H, Zinner M J, Ashley S W, Whang E E. Systemic siRNA-mediated gene silencing: a new approach to targeted therapy of cancer. Ann Surg 2004f; 240:667-74; discussion 75-6.

Eisenberg, D.; E. Schwarz; M. Komaromy & R. Wall (1984) Analysis of membrane and surface protein sequences with the hydrophobic moment plot. J Mol Biol, 179, 125-142

Els Conrath K, Lauwereys M, Wyns L, Muyldermans S. Camel single-domain antibodies as modular building units in bispecific and bivalent antibody constructs. J Biol Chem 2001; 276:7346-50.

Fedarovich A, Tomberg J, Nicholas R A, Davies C. Structure of the N-terminal domain of human CEACAM1: binding target of the opacity proteins during invasion of *Neisseria meningitidis* and *N. gonorrhoeae*. Acta Crystallogr D Biol Crystallogr 2006; 62:971-9.

Giannopoulos G, Pavlakis K, Parasi A, et al. The Expression of Matrix Metalloproteinases-2 and -9 and their Tissue Inhibitor 2 in Pancreatic Ductal and Ampullary Carcinoma and their Relation to Angiogenesis and Clinicopathological Parameters. Anticancer Research 2008; 28:1875-81.

Hamers-Casterman, C., Atarhouch, T., Muyldermans, S., Robinson, G., Hamers, C., Songa, E. B., Bendahman, N. and Hamers, R. Naturally occurring antibodies devoid of light chains. Nature 363, 446-448 (1993).

Han F, Zhu H-G. Caveolin-1 Regulating the Invasion and Expression of Matrix Metalloproteinase (MMPs) in Pancreatic Carcinoma Cells. The Journal of surgical research 2010; 159:443-50.

Haq M, Shafii A, Zervos E E, Rosemurgy A S. Addition of matrix metalloproteinase inhibition to conventional cytotoxic therapy reduces tumor implantation and prolongs survival in a murine model of human pancreatic cancer. Cancer Res 2000; 60:3207-11.

Iqbal, U., Trojahn, U., Albaghdadi, H., Zhang, J., O'Connor, M., Stanimirovic, D., Tomanek, B., Sutherland, G. and Abulrob, A. (2010) Kinetic analysis of novel mono- and multivalent VHH-fragments and their application for molecular targeting of brain tumors. British Journal of Pharmacology (in press).

Jespers, L., Schon, O., Famm, K. and Winter, G. Aggregation-resistant domain antibodies selected on phage by heat denaturation. Nat. Biotechnol. 22, 1161-1165 (2004).

Kabat E A, Wu T T. Identical V region amino acid sequences and segments of sequences in antibodies of different specificities. Relative contributions of VH and VL genes, minigenes, and complementary-determining regions to binding of antibody-combining sites. J Immunol. 1991; 147: 1709-19.

Kabat E A, Wu, T. T, Perry, H. M, Gottesman, K. S. and Koeler, C. Sequences of proteins of immunological interest. Publication 1991:91-3242.

Kessenbrock K, Plaks V, Werb Z. Matrix Metalloproteinases: Regulators of the Tumor Microenvironment. Cell 2010; 141:52-67. Lefranc, M.-P. et al., (2003) Dev. Comp. Immunol., 27, 55-77.

Kunnumakkara A B, Sung B, Ravindran J, et al. {Gamma}-tocotrienol inhibits pancreatic tumors and sensitizes them to gemcitabine treatment by modulating the inflammatory microenvironment. Cancer Res 2010; 70:8695-705.

Lefranc, M.-P., Pommié, C., Ruiz, M., Giudicelli, V., Foulquier, E., Truong, L., Thouvenin-Contet, V. and Lefranc, G. "IMGT unique numbering for immunoglobulin and T cell receptor variable domains and Ig superfamily V-like domains". Dev. Comp. Immunol., 27, 55-77 (2003)

Lewis-Wambi J S, Cunliffe H E, Kim H R, Willis A L, Jordan V C. Overexpression of CEACAM6 promotes migration and invasion of oestrogen-deprived breast cancer cells. Eur J Cancer 2008; 44:1770-9.

Li S, Zheng W, Kuolee R, Hirama T, Henry M, Makvandi-Nejad S, Fjallman T, Chen W, Zhang J. Pentabody-mediated antigen delivery induces antigen-specific mucosal immune response. Mol Immunol 2009; 46:1718-26.

Merritt, E. A. and Hol, W. G. AB5 toxins. Current Opinion in Structural Biology 5, 165-171 (1995).

Mosmann T. Rapid colorimetric assay for cellular growth and survival: application to proliferation and cytotoxicity assays. J Immunol Methods 1983; 65:55-63.

Nielsen, U. B., Adams, G. P., Weiner, L. M. and Marks, J. D. Targeting of bivalent anti-ErbB2 diabody antibody fragments to tumor cells is independent of the intrinsic antibody affinity. Cancer Research 60, 6434-6440 (2000).

Nuttall, S. D., Krishnan, U. V., Doughty, L., Pearson, K., Ryan, M. T., Hoogenraad, N. J., Hattarki, M., Carmichael, J. A., Irving, R. A. and Hudson, P. J. Isolation and characterization of an IgNAR variable domain specific for the human mitochondrial translocase receptor Tom70. Eur. J. Biochem. 270, 3543-3554 (2003).

Ordonez C, Screaton R A, Ilantzis C, Stanners C P. Human carcinoembryonic antigen functions as a general inhibitor of anoikis. Cancer Res 2000; 60:3419-24.

Ridgway J B B, Presta L G, Carter P. "Knobs-into-holes" engineering of antibody CH3 domains for heavy chain heterodimerization. Prot Eng 1996; 9:617-621

Schwarz R E, Konduri S, Awasthi N, Cafasso D, Schwarz M A. An antiendothelial combination therapy strategy to increase survival in experimental pancreatic cancer. Surgery 2009; 146:241-9.

Semenza G L. Targeting HIF-1 for cancer therapy. Nat Rev Cancer 2003; 3:721-32.

Strickland L A, Ross J, Williams S, Ross S, Romero M, Spencer S, Erickson R, Sutcliffe J, Verbeke C, Polakis P, van Bruggen N, Koeppen H. Preclinical evaluation of carcinoembryonic cell adhesion molecule (CEACAM) 6 as potential therapy target for pancreatic adenocarcinoma. J Pathol 2009; 218:380-90.

To, R., Hirama, T., Arbabi-Ghahroudi, M., MacKenzie, R., Wang, P., Xu, P., Ni, F. and Tanha, J. Isolation of monomeric human $V_H$s by a phage selection. J. Biol. Chem. 280, 41395-41403 (2005).

Vogel C L, Cobleigh M A, Tripathy D, Gutheil J C, Harris L N, Fehrenbacher L, Slamon D J, Murphy M, Novotny W F, Burchmore M, Shak S, Stewart S J. First-line Herceptin monotherapy in metastatic breast cancer. Oncology 2001; 61 Suppl 2:37-42.

Wang Z, Kong D, Banerjee S, et al. Down-regulation of Platelet-Derived Growth Factor-D Inhibits Cell Growth and Angiogenesis through Inactivation of Notch-1 and Nuclear Factor-kapaB Signaling. Cancer Research 2007; 67:11377-85.

Zhang, J., Li, Q., Nguyen, T.-D., Tremblay, T.-L., Stone, E., To, R., Kelly, J. and MacKenzie, C. R. A pentavalent single-domain antibody approach to tumor antigen discovery and the development of novel proteomics reagents. J. Mol. Biol. 341, 161-169 (2004a).

Zhang, J., Tanha, J., Hirama, T., Khieu, N. H., To, R., Tong-Sevinc, H., Stone, E., Brisson, J.-R. and MacKenzie, C. R. Pentamerization of single-domain antibodies from phage libraries: A novel strategy for the rapid generation of high-avidity antibody reagents. J. Mol. Biol. 335, 49-56 (2004b).

Zhang J, MacKenzie R, Durocher Y. Production of chimeric heavy-chain antibodies. Methods Mol Biol 2009a; 525: 323-36, xv.

Zhang J, Liu X, Bell A, et al. Transient expression and purification of chimeric heavy chain antibodies. Protein Expr Purif 2009b; 65:77-82.

U.S. Pat. No. 6,180,370
U.S. Pat. No. 5,693,761
U.S. Pat. No. 6,054,297
U.S. Pat. No. 5,859,205
U.S. Pat. No. 5,869,619
U.S. Pat. No. 5,766,886
U.S. Pat. No. 5,821,123
European Patent No. 519596
European Patent No. 626390
WO 95/04069
WO 2004/076670
WO 2003/046560

The invention claimed is:

1. A recombinant antibody or fragment thereof specific for CEACAM6, wherein the antibody or fragment thereof binds to an epitope consisting of the sequence NRIGYSWYKG (SEQ ID NO: 7).

2. A single domain antibody, comprising
a complementarity determining region (CDR) 1 comprising the sequence of GRTNSVYTMG (SEQ ID NO:1);
a CDR2 comprising the sequence of IMWGAGTNTHYADSVKG (SEQ ID NO:2); and
a CDR3 comprising the sequence of AANRGIPIAGRQYDY (SEQ ID NO:3), wherein the single domain antibody is specific for CEACAM6.

3. The single domain antibody of claim 2, wherein the antibody comprises the sequence:

(SEQ ID NO: 4)
QVKLEESGGGLVQAGGSLRLSCRTSGRTNSVYTMGWFRQAPGKEREFVAQ

IMWGAGTNTHYADSVKGRFTISRDSAESTVYLQMNSLKPEDTAVYYCAAN

RGIPIAGRQYDYWGQGTQVTVSS, or a sequence at least 90% identical thereto.

4. The single domain antibody of claim 2, wherein the antibody binds to an epitope comprising the sequence NRIGYSWYKG (SEQ ID NO:7).

5. The single domain antibody of claim 2, wherein the antibody is in a multivalent display.

6. The single domain antibody of claim 5, wherein the antibody is linked to a Fc fragment.

7. The single domain antibody of claim 6, wherein the Fc fragment is the mouse Fc2b or human Fc1.

8. The single domain antibody of claim 2, wherein the antibody is linked to a cargo molecule.

9. The single domain antibody of claim 8, wherein the cargo molecule is a therapeutic molecule.

10. The single domain antibody of claim 8, wherein the cargo molecule is a diagnostic agent.

11. The single domain antibody of claim 2, wherein the antibody is immobilized onto a surface.

12. A nucleic acid molecule encoding the single domain antibody of claim 2.

13. A vector comprising the nucleic acid molecule of claim 12.

14. An in vitro method of blocking CEACAM6 and decreasing its invasiveness, comprising contacting cells expressing CEACAM6 with the antibody of claim 2 or a multivalent display thereof, or a combination thereof.

15. An in vitro method of reducing cell proliferation, invasion, and MMP-9 activity, comprising contacting cells expressing CEACAM6 with the antibody of claim 2 or a multivalent display thereof, or a combination thereof.

16. An in vitro method of reducing the ability of tumor cells to promote angiogenesis, comprising contacting cells expressing CEACAM6 with the antibody of claim 2 or a multivalent display thereof, or a combination thereof.

17. An in vivo method of detecting CEACAM6-expressing tumors, comprising:
   a) administering the single domain antibody of claim 10 to a subject; and
   b) detecting the binding of the single domain antibody.

18. The in vivo method of claim 17, wherein the diagnostic agent is a radioisotope, a paramagnetic label, a fluorophore, a Near Infra-Red (NIR) fluorochrome or dye, an affinity label, or a detectable protein-based molecule.

19. The in vivo method of claim 17, wherein the step of detecting (step b)) is accomplished by non-invasive optical imaging, ultrasound, MRI, PET, or SPECT.

20. An in vitro method of detecting CEACAM6-expressing tumors, comprising:
   a) contacting a tumor sample with the single domain antibody of claim 10; and
   b) detecting the binding of the single domain antibody.

21. The in vitro method of claim 20, wherein the diagnostic agent is a fluorescent dye or an enzyme.

22. The in vitro method of claim 20, wherein the diagnostic agent is FITC or Enhanced Green Fluorescent Protein (EGFP).

23. The in vitro method of claim 20, wherein the step of detecting (step b)) is accomplished by immunofluorescence staining or immunohistochemistry.

* * * * *

SEQUENCE LISTING

```
<160> NUMBER OF SEQ ID NOS: 16

<210> SEQ ID NO 1
<211> LENGTH: 10
<212> TYPE: PRT
<213> ORGANISM: Artificial Sequence
<220> FEATURE:
<223> OTHER INFORMATION: CDR1

<400> SEQUENCE: 1

Gly Arg Thr Asn Ser Val Tyr Thr Met Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR2

<400> SEQUENCE: 2

Ile Met Trp Gly Ala Gly Thr Asn Thr His Tyr Ala Asp Ser Val Lys
1               5                   10                  15

Gly
```

```
<210> SEQ ID NO 3
<211> LENGTH: 15
<212> TYPE: PRT
<213> ORGANISM: Artificial Sequence
<220> FEATURE:
<223> OTHER INFORMATION: CDR3

<400> SEQUENCE: 3

Ala Ala Asn Arg Gly Ile Pro Ile Ala Gly Arg Gln Tyr Asp Tyr
1               5                   10                  15

<210> SEQ ID NO 4
<211> LENGTH: 123
<212> TYPE: PRT
<213> ORGANISM: Artificial Sequence
<220> FEATURE:
<223> OTHER INFORMATION: Anti-CEACAM6 sdAb

<400> SEQUENCE: 4

Gln Val Lys Leu Glu Glu Ser Gly Gly Gly Leu Val Gln Ala Gly Gly
1               5                   10                  15

Ser Leu Arg Leu Ser Cys Arg Thr Ser Gly Arg Thr Asn Ser Val Tyr
                20                  25                  30

Thr Met Gly Trp Phe Arg Gln Ala Pro Gly Lys Glu Arg Glu Phe Val
            35                  40                  45

Ala Gln Ile Met Trp Gly Ala Gly Thr Asn Thr His Tyr Ala Asp Ser
        50                  55                  60

Val Lys Gly Arg Phe Thr Ile Ser Arg Asp Ser Ala Glu Ser Thr Val
65                  70                  75                  80

Tyr Leu Gln Met Asn Ser Leu Lys Pro Glu Asp Thr Ala Val Tyr Tyr
                85                  90                  95

Cys Ala Ala Asn Arg Gly Ile Pro Ile Ala Gly Arg Gln Tyr Asp Tyr
            100                 105                 110

Trp Gly Gln Gly Thr Gln Val Thr Val Ser Ser
        115                 120

<210> SEQ ID NO 5
<211> LENGTH: 15
<212> TYPE: PRT
<213> ORGANISM: Artificial Sequence
<220> FEATURE:
<223> OTHER INFORMATION: CEACAM6 peptide

<400> SEQUENCE: 5

His Asn Leu Pro Gln Asn Arg Ile Gly Tyr Ser Trp Tyr Lys Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: CEACAM6 peptide

<400> SEQUENCE: 6

Asn Arg Ile Gly Tyr Ser Trp Tyr Lys Gly Glu Arg Val Asp Gly
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: CEACAM6 epitope
```

<400> SEQUENCE: 7

Asn Arg Ile Gly Tyr Ser Trp Tyr Lys Gly
1               5                   10

<210> SEQ ID NO 8
<211> LENGTH: 344
<212> TYPE: PRT
<213> ORGANISM: Human

<400> SEQUENCE: 8

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 9
<211> LENGTH: 45
<212> TYPE: DNA
<213> ORGANISM: Artificial Sequence
<220> FEATURE:
<223> OTHER INFORMATION: Primer

<400> SEQUENCE: 9
gcccagccgg ccatggccsm kgtgcagctg gtggaktctg gggga         45

<210> SEQ ID NO 10
<211> LENGTH: 45
<212> TYPE: DNA
<213> ORGANISM: Artificial Sequence
<220> FEATURE:
<223> OTHER INFORMATION: Primer

<400> SEQUENCE: 10
gcccagccgg ccatggccca ggtaaagctg gaggagtctg gggga         45

<210> SEQ ID NO 11
<211> LENGTH: 45
<212> TYPE: DNA
<213> ORGANISM: Artificial Sequence
<220> FEATURE:
<223> OTHER INFORMATION: Primer

<400> SEQUENCE: 11
gcccagccgg ccatggccca ggctcaggta cagctggtgg agtct         45

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cgccatcaag gtaccagttg a                                    21

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
ggggtacctg tcatccacgg accagctga                            29

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
catgtgtaga ctcgcggccc agccggccat ggcc                      34

<210> SEQ ID NO 15
<211> LENGTH: 47
<212> TYPE: DNA
<213> ORGANISM: Artificial Sequence
<220> FEATURE:

```
<223> OTHER INFORMATION: Primer

<400> SEQUENCE: 15
catgtgtaga ttcctggccg gcctggcctg aggagacggt gacctgg        47

<210> SEQ ID NO 16
<211> LENGTH: 173
<212> TYPE: PRT
<213> ORGANISM: Artificial Sequence
<220> FEATURE:
<223> OTHER INFORMATION: Anti-CEACAM6 sdAb

<400> SEQUENCE: 16

Met Lys Lys Thr Ala Ile Ala Ile Ala Val Ala Leu Ala Gly Phe Ala
1               5                   10                  15

Thr Val Ala Gln Ala Gln Pro Ala Met Ala Gln Val Lys Leu Glu Glu
            20                  25                  30

Ser Gly Gly Gly Leu Val Gln Ala Gly Gly Ser Leu Arg Leu Ser Cys
        35                  40                  45

Arg Thr Ser Gly Arg Thr Asn Ser Val Tyr Thr Met Gly Trp Phe Arg
    50                  55                  60

Gln Ala Pro Gly Lys Glu Arg Glu Phe Val Ala Gln Ile Met Trp Gly
65                  70                  75                  80

Ala Gly Thr Asn Thr His Tyr Ala Asp Ser Val Lys Gly Arg Phe Thr
                85                  90                  95

Ile Ser Arg Asp Ser Ala Glu Ser Thr Val Tyr Leu Gln Met Asn Ser
            100                 105                 110

Leu Lys Pro Glu Asp Thr Ala Val Tyr Tyr Cys Ala Ala Asn Arg Gly
        115                 120                 125

Ile Pro Ile Ala Gly Arg Gln Tyr Asp Tyr Trp Gly Gln Gly Thr Gln
    130                 135                 140

Val Thr Val Ser Ser Gly Gln Ala Gly Gln Gly Ser Glu Gln Lys Leu
145                 150                 155                 160

Ile Ser Glu Glu Asp Leu Asn His His His His His
                165                 170
```